(12) United States Patent
Kamimura et al.

(10) Patent No.: US 11,958,005 B2
(45) Date of Patent: Apr. 16, 2024

(54) CHEMICAL LIQUID PURIFICATION METHOD AND CHEMICAL LIQUID

(71) Applicant: FUJIFILM Corporation, Tokyo (JP)

(72) Inventors: Tetsuya Kamimura, Haibara-gun (JP); Masahiro Yoshidome, Haibara-gun (JP); Yukihisa Kawada, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/957,408

(22) Filed: Sep. 30, 2022

(65) Prior Publication Data

US 2023/0087746 A1  Mar. 23, 2023

Related U.S. Application Data

(60) Division of application No. 16/778,705, filed on Jan. 31, 2020, now Pat. No. 11,491,428, which is a (Continued)

(30) Foreign Application Priority Data

Aug. 31, 2017 (JP) .................................. 2017-167319

(51) Int. Cl.
*B01D 37/04* (2006.01)
*B01D 19/04* (2006.01)
(Continued)

(52) U.S. Cl.
CPC ......... *B01D 37/04* (2013.01); *B01D 19/0404* (2013.01); *B01D 27/00* (2013.01); (Continued)

(58) Field of Classification Search
CPC .... B01D 37/04; B01D 27/00; B01D 39/1676; B01D 39/16; B01D 39/00; B01D 2257/60;
(Continued)

(56) References Cited

U.S. PATENT DOCUMENTS 6,187,965 B1    2/2001  Bhatt et al.
2004/0011638 A1  1/2004  Lepizzera
(Continued)

FOREIGN PATENT DOCUMENTS

CN    1531521 A    9/2004
CN    104781384 A    7/2015
(Continued)

OTHER PUBLICATIONS

JP 2009132756 A English description; Uchimura Tatsuji et al., Jun. 2009.*
(Continued)

*Primary Examiner* — Akash K Varma
(74) *Attorney, Agent, or Firm* — Sughrue Mion, PLLC

(57) ABSTRACT

An object of the present invention is to provide a chemical liquid purification method which makes it possible to obtain a chemical liquid having excellent defect inhibition performance. Another object of the present invention is to provide a chemical liquid. The chemical liquid purification method according to an embodiment of the present invention is a chemical liquid purification method including obtaining a chemical liquid by purifying a substance to be purified containing an organic solvent, in which a content of the stabilizer in the substance to be purified with respect to the total mass of the substance to be purified is equal to or greater than 0.1 mass ppm and less than 100 mass ppm.

6 Claims, 4 Drawing Sheets

Related U.S. Application Data continuation of application No. PCT/JP2018/031979, filed on Aug. 29, 2018.

(51) Int. Cl.
| | | |
|---|---|---|
| *B01D 27/00* | (2006.01) | |
| *B01D 39/16* | (2006.01) | |
| *B01D 53/46* | (2006.01) | |
| *B01J 31/00* | (2006.01) | |
| *B01J 31/06* | (2006.01) | |
| *B01J 47/014* | (2017.01) | |

(52) U.S. Cl.
CPC ......... *B01D 39/1676* (2013.01); *B01D 53/46* (2013.01); *B01J 31/00* (2013.01); *B01J 31/063* (2013.01); *B01J 47/014* (2017.01); *B01D 2257/60* (2013.01)

(58) Field of Classification Search
CPC .... B01D 19/0404; B01D 19/04; B01D 61/14; B01D 11/0415; B01D 15/00; B01D 53/46; B01J 47/014; B01J 47/00; B01J 31/00; B01J 31/063; B01J 31/06; H01L 21/304; G03F 7/004; G03F 7/16; G03F 7/30; G03F 7/0048; C07B 63/00; C07B 63/04; C07C 7/20; C07C 7/00; C07C 9/14; C07C 29/94; C07C 29/74; C07C 31/10; C07C 41/46; C07C 41/34; C07C 43/04; C07C 43/13; C07C 45/78; C07C 45/86; C07C 49/04; C07C 49/395; C07C 49/403; C07C 67/62; C07C 67/48; C07C 69/14; C07C 69/68; C07C 69/708; C07D 307/33; C11D 7/50; C02F 1/28; C02F 1/42
USPC ................................................ 210/638, 749
See application file for complete search history.

(56) References Cited

U.S. PATENT DOCUMENTS

| | | |
|---|---|---|
| 2014/0162403 A1 | 6/2014 | Okabe et al. |
| 2015/0240089 A1 | 8/2015 | Mitsuoka et al. |
| 2017/0285482 A1 | 10/2017 | Tsuchihashi et al. |
| 2018/0187134 A1 | 7/2018 | Nakamura et al. |
| 2019/0171102 A1 | 6/2019 | Kamimura et al. |
| 2020/0164294 A1 | 5/2020 | Kamimura et al. |

FOREIGN PATENT DOCUMENTS

| | | | | |
|---|---|---|---|---|
| JP | 10-036893 A | | 2/1998 | |
| JP | 2000-290224 A | | 10/2000 | |
| JP | 2000290224 A | * | 10/2000 | ............. C07C 51/64 |
| JP | 2001-125277 A | | 5/2001 | |
| JP | 2001125277 A | * | 5/2001 | |
| JP | 2004-197140 A | | 7/2004 | |
| JP | 2009-132756 A | | 6/2009 | |
| JP | 2009132756 A | * | 6/2009 | ............. C08G 64/24 |
| JP | WO2013/015322 A1 | | 1/2013 | |
| JP | 2016-073922 A | | 5/2016 | |
| KR | 10-2000-0035014 A | | 6/2000 | |
| TW | 201627780 A | | 8/2016 | |
| WO | 2017/038933 A1 | | 3/2017 | |
| WO | 2018/043690 A1 | | 3/2018 | |
| WO | 2018/051716 A1 | | 3/2018 | |

OTHER PUBLICATIONS

JP 2001125277 A English description; Tsubata et al., May 2001.*
JP 2000290224 A Enligh description; Kaneko et al., Oct. 2000.*
International Search Report dated Oct. 30, 2018 from the International Searching Authority in International Application No. PCT/JP2018/031979.
Communication dated May 3, 2021 from the Korean Intellectual Property Office in Korean Application No. 10-2020-7001631.
Office Action dated Mar. 8, 2022 from the Taiwanese Intellectual Property Office in TW Application No. 107130211.
International Preliminary Report on Patentability dated Mar. 3, 2020 from the International Bureau in International Application No. PCT/JP2018/031979.
Office Action dated Dec. 3, 2021 in Taiwanese Application No. 107130211.
Written Opinion dated Oct. 30, 2018 from the International Bureau in International Application No. PCT/JP2018/031979.
Communication dated May 14, 2021 from The State Intellectual Property Office of PR of China in Chinese Application No. 201880052684.6.
Office Action dated Nov. 4, 2020 from the China National Intellectual Property Administration in Chinese Application No. 201880052684.6.
JP 2001125277 A English description, May 2001, Tsubata Yoshiaki et al.
JP 2000290224 A English description, Oct. 2000, Kaneko Akira et al.
JP 2009132756 A English description, Jun. 2009, Uchimura Tatsuji et al.

* cited by examiner

CHEMICAL LIQUID PURIFICATION METHOD AND CHEMICAL LIQUID

CROSS-REFERENCE TO RELATED APPLICATIONS

This application is a divisional application of application Ser. No. 16/778,705 filed Jan. 31, 2020, which is a Continuation of PCT International Application No. PCT/JP2018/031979 filed on Aug. 29, 2018, which claims priority under 35 U.S.C. § 119(a) to Japanese Patent Application No. 2017-167319 filed on Aug. 31, 2017. Each of the above applications is hereby expressly incorporated by reference, in its entirety, into the present application.

BACKGROUND OF THE INVENTION

1. Field of the Invention

The present invention relates to a chemical liquid purification method and a chemical liquid.

2. Description of the Related Art

In a case where semiconductor devices are manufactured by a wiring forming process including photolithography, as a prewet solution, a resist solution, a developer, a rinsing solution, a peeling solution, a Chemical Mechanical Polishing (CMP) slurry, a washing solution used after CMP, and the like, a chemical liquid containing a solvent (typically, an organic solvent) is used. In recent years, the manufacturing of semiconductor devices at a node equal to or smaller than 10 nm has been examined. Accordingly, the inhibition of adhesion of particles to a semiconductor wafer is strongly required, and the aforementioned chemical liquid is also required to prevent particles from easily adhering to a semiconductor wafer in each process.

Therefore, as the aforementioned chemical liquid, a chemical liquid is used which is obtained by purifying a substance to be purified (for example, a substance to be purified containing an organic solvent) such that the amount of substances causing particles is reduced.

JP2001-125277A describes "a method for manufacturing a photoresist solution with a reduced amount of impurities, including passing a photoresist solution through a column filled with a substance capable of adsorbing metal impurities, leading the photoresist solution having passed through the column back to the column, and circulating the photoresist solution in a closed system such that metal impurities in the photoresist solution are removed".

SUMMARY OF THE INVENTION

The inventors of the present invention examined a photoresist solution manufactured using the manufacturing method described in JP2001-125277A. As a result, the inventors have found that the photoresist solution has a problem with defect inhibition performance.

An object of the present invention is to provide a chemical liquid purification method which makes it possible to obtain a chemical liquid having excellent defect inhibition performance. Another object of the present invention is to provide a chemical liquid.

In order to achieve the aforementioned objects, the inventors of the present invention carried out an intensive examination. As a result, the inventors have found that the objects can be achieved by the following constitution.

[1] A chemical liquid purification method, including obtaining a chemical liquid by purifying a substance to be purified containing an organic solvent, in which a content of a stabilizer in the substance to be purified with respect to a total mass of the substance to be purified is equal to or greater than 0.1 mass ppm and less than 100 mass ppm.

[2] The chemical liquid purification method described in [1], in which the substance to be purified contains water, and a content of water in the substance to be purified with respect to the total mass of the substance to be purified is 500 to 50,000 mass ppm.

[3] The chemical liquid purification method described in [1] or [2], in which the substance to be purified contains at least one kind of metal ions selected from the group consisting of Fe, Cr, Pb, and Ni, in a case where the substance to be purified contains one kind of metal ions, a content of the metal ions with respect to the total mass of the substance to be purified is 1.0 to 10,000 mass ppt, and in a case where the substance to be purified contains two or more kinds of metal ions, a content of each of the metal ions with respect to the total mass of the substance to be purified is 1.0 to 10,000 mass ppt.

[4] The chemical liquid purification method described in any one of [1] to [3], in which the substance to be purified contains at least one kind of metal particles selected from the group consisting of Fe, Cr, Pb, and Ni, in a case where the substance to be purified contains one kind of metal particles, a content of the metal particles with respect to the total mass of the substance to be purified is 1.0 to 10,000 mass ppt, and in a case where the substance to be purified contains two or more kinds of metal particles, a content of each of the metal particles with respect to the total mass of the substance to be purified is 1.0 to 10,000 mass ppt.

[5] The chemical liquid purification method described in any one of [1] to [4], in which the substance to be purified is purified by at least one kind of method selected from the group consisting of ion adsorption, ion exchange, and filtration.

[6] The chemical liquid purification method described in any one of [1] to [5], in which the stabilizer is at least one kind of compound selected from the group consisting of a compound represented by Formula (1), a compound represented by Formula (2), and 2-methyl-2-butene.

[7] A chemical liquid purified by the purification method described in any one of [1] to [6].

[8] A chemical liquid purified by the purification method described in any one of [1] to [6], containing an organic solvent, a stabilizer, at least one kind of metal ions selected from the group consisting of Fe, Cr, Pb, and Ni, and at least one kind of metal particles selected from the group consisting of Fe, Cr, Pb, and Ni, in which a content of the stabilizer in the chemical liquid with respect to a total mass of the chemical liquid is 0.1 to 50 mass ppm, in a case where the chemical liquid contains one kind of metal ions, a content of the metal ions with respect to the total mass of the chemical liquid is equal to or smaller than 100 mass ppt, in a case where the chemical liquid contains two or more kinds of metal ions, a content of each of the metal ions with respect to the total mass of the chemical liquid is equal to or smaller than 100 mass ppt, in a case where the chemical liquid contains one kind of metal particles, a content of the metal particles with respect to the total mass of the chemical liquid is equal to or smaller than 100 mass ppt, and in a case where the chemical liquid contains two or more kinds of metal particles, a content of each of the metal particles with respect to the total mass of the chemical liquid is equal to or smaller than 100 mass ppt.

According to the present invention, a chemical liquid purification method which makes it possible to obtain a chemical liquid having excellent defect inhibition performance can be provided. Furthermore, according to the present invention, it is possible to provide a chemical liquid.

DESCRIPTION OF THE PREFERRED EMBODIMENTS

Figure 1:
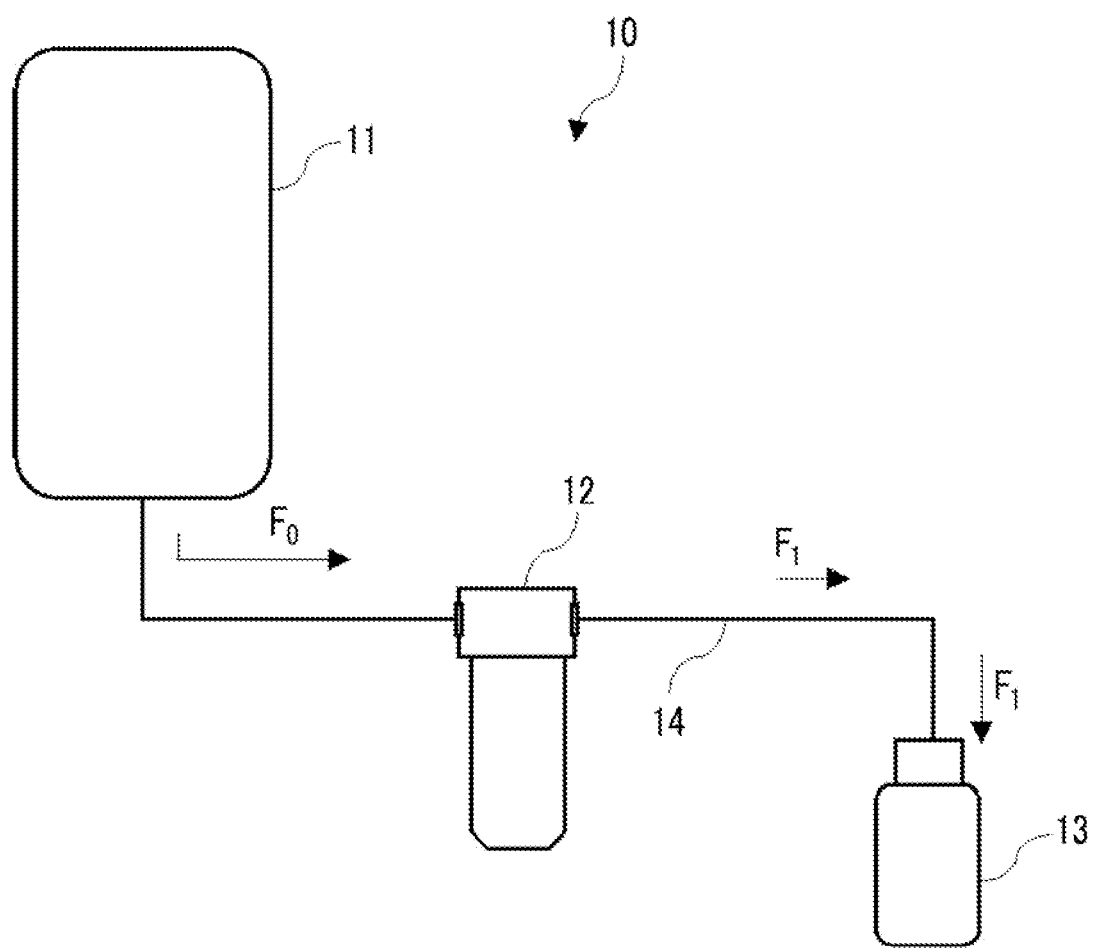
FIG. 1 is a schematic view of a typical filtering device that can be used for filtering a substance to be purified.

Hereinafter, the present invention will be specifically described.

The following constituents will be described based on typical embodiments of the present invention in some cases, but the present invention is not limited to the embodiments.

In the present specification, a range of numerical values described using "to" means a range including the numerical values listed before and after "to" as a lower limit and an upper limit respectively.

In the present invention, "preparation" means not only the preparation of a specific material by means of synthesis or mixing but also the preparation of a predetermined substance by means of purchase and the like.

In the present invention, "ppm" means "parts-per-million ($10^{-6}$)", "ppb" means "parts-per-billion ($10^{-9}$)", "ppt" means "parts-per-trillion ($10^{-12}$)", and "ppq" means "parts-per-quadrillion ($10^{-15}$)".

In the present invention, regarding the description of a group (atomic group), in a case where whether the group is substituted or unsubstituted is not described, as long as the effects of the present invention are not impaired, the group includes a group which does not have a substituent and a group which has a substituent. For example, "hydrocarbon group" includes not only a hydrocarbon group which does not have a substituent (unsubstituted hydrocarbon group) but also a hydrocarbon group which has a substituent (substituted hydrocarbon group). The same is true for each compound.

Furthermore, in the present invention, "radiation" means, for example, far ultraviolet rays, extreme ultraviolet (EUV), X-rays, electron beams, and the like. In addition, in the present invention, "light" means actinic rays or radiation. In the present invention, unless otherwise specified, "exposure" includes not only exposure, far ultraviolet rays, X-rays, and EUV, and the like, but also lithography by particle beams such as Electron beams or ion beams.

[Chemical Liquid Purification Method]

The chemical liquid purification method described above is a chemical liquid purification method including obtaining a chemical liquid by purifying a substance to be purified containing an organic solvent, in which a content of a stabilizer in the substance to be purified with respect to the total mass of the substance to be purified is equal to or greater than 0.1 mass ppm and less than 100 mass ppm.

As described above, the chemical liquid used in a general wiring forming process including photolithography is required to have further improved defect inhibition performance. "The occurrence of defects" means the adhesion of particles to a wafer (hereinafter, described as "particle defects" as well) and the occurrence of stain-like abnormal sites on a wafer (hereinafter, described as "stain-like defects" as well). Both the occurrence of particle defects and occurrence of stain-like defects lead to a yield reduction in the manufacturing of semiconductor devices.

Generally, it is considered that the particle defects and the stain-like defects may occur due to the impurities, particularly, the metal impurities contained in the chemical liquid. Therefore, many methods for removing metal impurities contained in the chemical liquid as described in JP2001-125277A have been developed.

Even though a chemical liquid is obtained by removing metal impurities contained in a substance to be purified as described in JP2001-125277A, a sufficient defect inhibition performance, particularly, a performance for inhibiting the occurrence of stain-like defects is not necessarily obtained in some cases. The inventors of the present invention consider that other trace components contained in the chemical liquid may cause the above phenomenon. As a result of analyzing various trace components in the chemical liquid, the inventors of the present invention have found that the chemical liquid contains a certain amount of stabilizer. Therefore, the inventors reexamined the entire process of obtaining the chemical liquid from the substance to be purified, and continuously investigated how the stabilizer is mixed into the chemical liquid.

Generally, a stabilizer is added to commercial organic solvents in many cases so as to maintain the quality of the organic solvents. It is known that in a case where a chemical liquid is obtained by purifying a substance to be purified containing such organic solvents, the chemical liquid also contains the stabilizer. By the inventors of the present invention, for the first time, it has been revealed that the stabilizer causes stain-like defects.

The inventors of the present invention distilled the substance to be purified containing the organic solvents so as to thoroughly remove the stabilizer, then obtained a chemical liquid by further filtering the substance to be purified, and applied the chemical liquid to photolithography. As a result, although the occurrence of stain-like defects was inhibited, particle defects occurred contrary to expectations.

In order to find out why defects of another form (particle defects) occurred in spite of thoroughly removing impurities (stabilizer) assumed to be as the cause of defects, the inventors of the present invention continued examination.

As a result, by the inventors of the present invention, for the first time, it has been revealed that in a case where the stabilizer is excessively removed from the substance to be purified, in the following process of purifying the substance to be purified, an extremely small fraction of the organic solvent is decomposed, a trace of decomposed product having a low molecular weight generated by the decomposition forms a complex by being bonded to metal ions contained in the substance to be purified, and the complex is likely to cause the particle defects.

Based on the findings of their own, the inventors of the present invention examined a chemical liquid purification method that can inhibit the occurrence of both the stain-like defects and particle defects. As a result, the inventors have found that the objects described above can be achieved in a case where the content of the stabilizer in the substance to be purified with respect to the total mass of the substance to be purified is equal to or greater than 0.1 mass ppm and less than 100 mass ppm, and have accomplished the present invention.

That is, in a case where the content of the stabilizer is equal to or greater than 0.1 mass ppm, the organic solvent is hardly decomposed in the process of purification. Consequently, the complex with metal ions is not easily formed, and hence the occurrence of particle defects is inhibited. In contrast, in a case where the content of the stabilizer is less than 100 mass ppm, the occurrence of stain-like defects resulting from the stabilizer is inhibited.

Hereinafter, the components of the substance to be purified to which the chemical liquid purification method can be applied will be described, and then each of the steps included in the chemical liquid purification method will be specifically described.

In the present specification, the defect inhibition performance of a chemical liquid is evaluated by a method using a wafer surface inspection device (SP-5; manufactured by KLA-Tencor Corporation.). Details of the procedure of the method are as described in Examples.

Defects are detected using this device according to the following principle. First, a wafer is coated with a chemical liquid, and the surface of the wafer coated with the chemical liquid is irradiated with a laser beam. In a case where the laser beam hits foreign substances and/or defects, light is scattered, the scattered light is detected by a detector, and the foreign substances and the defects are detected. Furthermore, in a case where the measurement is performed in a state of rotating the wafer during the irradiation with the laser beam, from the rotation angle of the wafer and the radial position of the laser beam, the coordinate locations of the foreign substances and the defects can be assigned.

In addition to SP-5 described above, an inspection device adopting the same measurement principle as SP-5 can be used for evaluating the defect inhibition performance of a chemical liquid. Examples of the inspection device include a Surfscan series manufactured by KLA-Tencor Corporation., and the like. Particularly, for evaluating the defect inhibition performance of a chemical liquid used for manufacturing micro-semiconductor devices at a node equal to or smaller than 10 nm, it is preferable to use "SP-5" described above or a wafer surface inspection device (typically, devices sequel to SP-5, or the like) having resolution equal to or higher than the resolution of "SP-5".

[Substance to be Purified]

The substance to be purified contains an organic solvent and a stabilizer. The content of the stabilizer with respect to the total mass of the substance to be purified is equal to or greater than 0.1 mass ppm and less than 100 mass ppm.

<Stabilizer>

The stabilizer contained in the substance to be purified is not particularly limited, and may be appropriately selected according to the type of the organic solvent contained in the substance to be purified.

The content of the stabilizer in the substance to be purified with respect to the total mass of the substance to be purified is equal to or greater than 0.1 mass ppm and less than 100 mass ppm. In view of obtaining a chemical liquid having further improved effects of the present invention, the content of the stabilizer is preferably 0.2 to 60 mass ppm, and more preferably 0.6 to 30 mass ppm. One kind of stabilizer may be used singly, or two or more kinds of stabilizers may be used in combination. In a case where two or more kinds of stabilizers are used in combination, the total content thereof is preferably within the above range.

The content of the stabilizer in the substance to be purified can be measured using a gas chromatography mass spectrometer, and the analysis conditions thereof and the like are as described in Examples.

As the stabilizer, in view of obtaining a chemical liquid having further improved effects of the present invention, at least one kind of compound selected from the group consisting of a compound represented by the following Formula (1), a compound represented by the following Formula (2), and 2-methyl-2-butene is preferable.

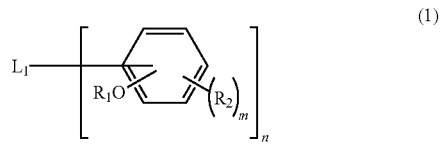

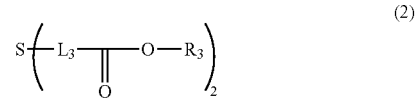

In Formula (1), m represents an integer of 1 to 4, and n represents an integer of 1 to 6. In a case where n is 1, $L_1$ represents a hydrogen atom, a hydroxyl group, or a monovalent organic group, $R_1$ represents a hydrogen atom, and $R_2$ represents a hydrogen atom, a hydroxyl group, or a monovalent organic group. A plurality of $R_2$'s may be the same as or different from each other. In a case where n is 2 to 6, $L_1$ represents an n-valent linking group, $R_1$ represents a hydrogen atom or a monovalent organic group. Although a plurality of $R_1$'s may be the same as or different from each other, at least one of $R_1$'s represents a hydrogen atom. $R_2$ represents a hydroxyl group or a monovalent organic group. A plurality of $R_2$'s may be the same as or different from each other.

In Formula (2), $L_3$ represents a single bond or a divalent linking group, and $R_3$ represents a monovalent organic group. A plurality of $L_3$'s and $R_3$'s may be the same as or different from each other respectively.

In a case where n in Formula (1) is 1, as the organic group represented by $L_1$, an alkyl group having 1 to 40 carbon atoms, an alkoxy group having 1 to 40 carbon atoms, an aryl group having 6 to 40 carbon atoms, an arylalkyl group having 7 to 40 carbon atoms, or a combination of these is preferable.

Examples of the monovalent organic group represented by $R_2$ include a hydrocarbon group having 1 to 40 carbon atoms that may have a heteroatom.

Particularly, in view of obtaining a chemical liquid having further improved effects of the present invention, in a case where n in Formula (1) is 1, $L_1$ is more preferably a hydrogen atom, an alkyl group having 1 to 6 carbon atoms, or a hydroxyl group, m is more preferably 2, and $R_2$ is more preferably a hydrogen atom or an alkyl group having 1 to 10 carbon atoms.

Examples of the stabilizer described above include the following compounds.

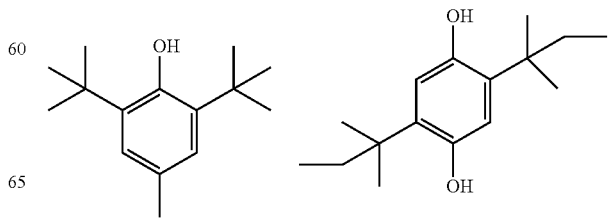

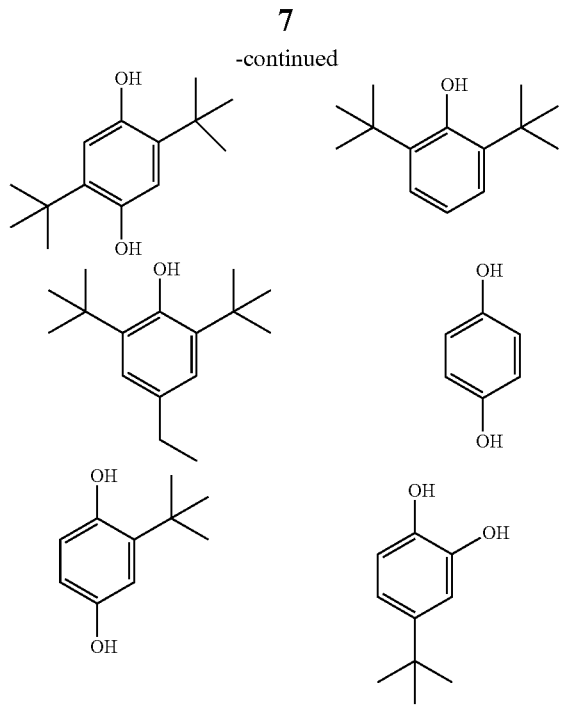

In a case where n in Formula (1) is 2, examples of the divalent linking group represented by $L_1$ include a divalent aliphatic hydrocarbon group (preferably having 1 to 8 carbon atoms), a divalent aromatic hydrocarbon group (preferably having 6 to 12 carbon atoms), —O—, —S—, —N(Rx)- (Rx: monovalent organic group), —C(=O)—, —C(=O)—O—, —O—C(=O)—O—, —C(=O)—NH—, —O—C(=O)—NH—, —S(=O)—, —S(=O)—O—, —S(=O)$_2$—, —S(=O)$_2$—O—, —CH=N—, a group obtained by combining these (for example, an alkyleneoxy group, an alkyleneoxycarbonyl group, an alkylenecarbonyloxy group), and the like.

Examples of the stabilizer described above include the following compounds.

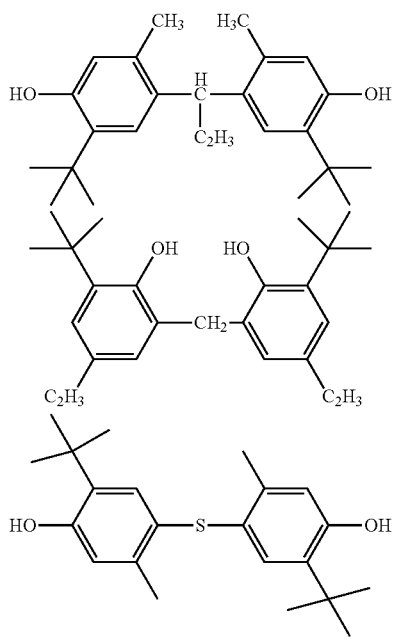

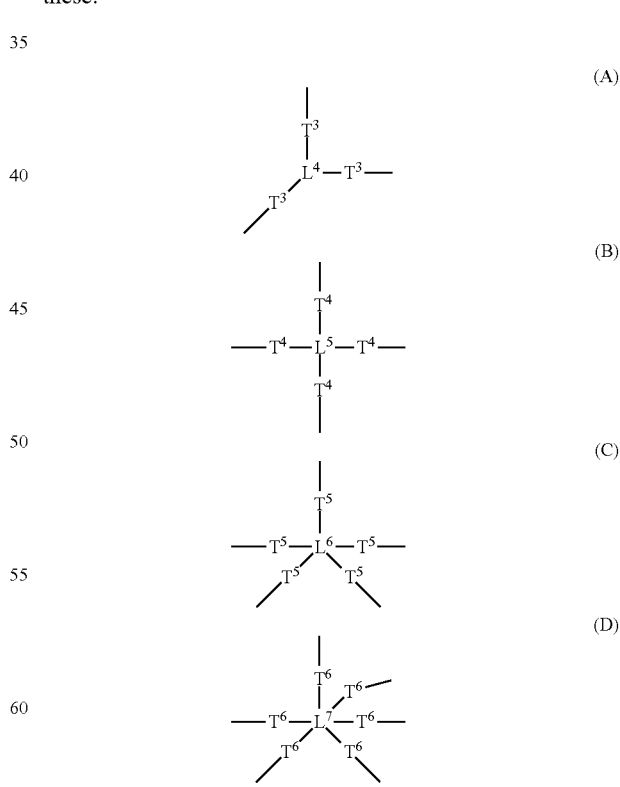

Commercial products of the stabilizer described above include "YOSHINOX BB (4,4'-butylidenebis-(6-t-butyl-3-methylphenol))" and "YOSHINOX 425 (2,2'-methylenebis-(4-ethyl-6-t-butylphenol))" manufactured by Mitsubishi Chemical Corporation, "SUMILIZER MDP-S (2,2'-Methylenebis(6-tert-butyl-4-methylphenol))", "SUMILIZER WX-R (4,4'-Thiobis(6-tert-butyl-3-methylphenol))", and "SUMILIZER WX-RC (4,4'-Thiobis(6-tert-butyl-3-methylphenol))" manufactured by Sumitomo Chemical Co., Ltd., and the like, but the present invention is not limited to these.

In a case where n in Formula (1) is 3 to 6, examples of the linking group having a valency of 3 to 6 represented by $L_1$ include a trivalent linking group such as a trimethylolpropane residue or an isocyanuric ring having three —(CH$_2$)$_k$— groups (k represents, for example, an integer of 2 to 6), a tetravalent or pentavalent linking group such as a pentaerythritol residue, a hexavalent linking group such as a dipentaerythritol residue, a combination of these, and the like.

The n-valent organic linking group represented by $L_1$ may be, for example, a group represented by any of the following Formulae (A) to (D) or a group obtained by combining these.

In Formulae (A) to (D), $L^4$ represents a trivalent group. $T^3$ represents a single bond or a divalent linking group, and three $T^3$'s may be the same as or different from each other.

L⁵ represents a tetravalent group. T⁴ represents a single bond or a divalent linking group, and four T⁴'s may be the same as or different from each other.

L⁶ represents a pentavalent group. T⁵ represents a single bond or a divalent linking group, and five T⁵'s may be the same as or different from each other.

L⁷ represents a hexavalent group. T⁶ represents a single bond or a divalent linking group, and six T⁶'s may be the same as or different from each other.

The divalent linking group represented by each of T³, T⁴, T⁵, and T⁶ has the same definition as the divalent linking group represented by L₁ described above.

Examples of the stabilizer described above include the following compounds.

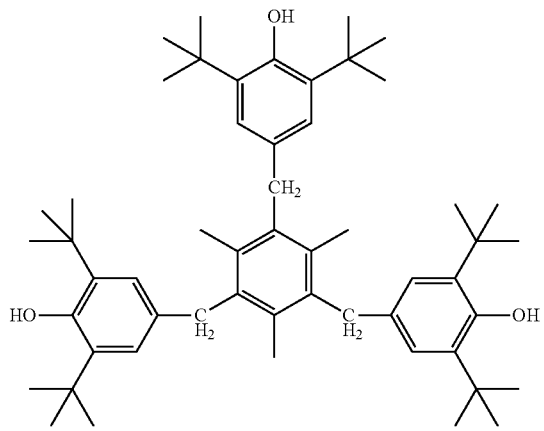

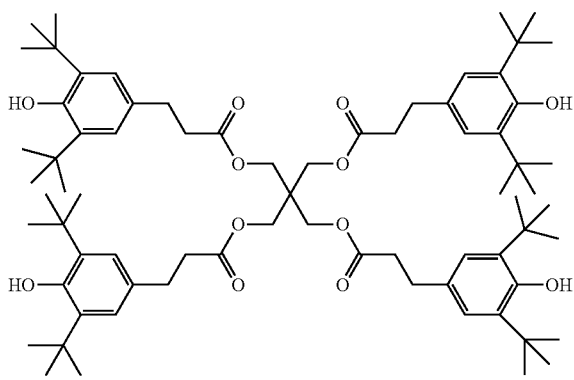

Examples of the divalent linking group in Formula (2) include those described above as the divalent linking group represented by L₁. Examples of the monovalent organic group represented by R₃ include a hydrocarbon group having 1 to 40 carbon atoms that may have a heteroatom. As the hydrocarbon group, an alkyl group is preferable. The number of carbon atoms in the alkyl group is preferably 1 to 30, and more preferably 5 to 20.

Examples of the stabilizer represented by Formula (2) include the following compounds and the like.

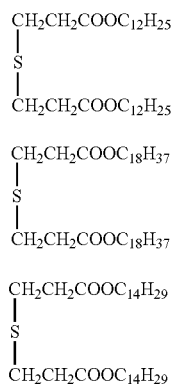

<Organic Solvent>

The substance to be purified contains an organic solvent. The content of the organic solvent in the substance to be purified is not particularly limited. Generally, the content of the organic solvent with respect to the total mass of the chemical liquid is preferably equal to or greater than 94.0% by mass, more preferably equal to or greater than 97.0% by mass, and even more preferably equal to or greater than 99.0% by mass. The upper limit thereof is not particularly limited, but is preferably equal to or smaller than 99.05% by mass in general.

One kind of organic solvent may be used single bond, or two or more kinds of organic solvents may be used in combination. In a case where two or more kinds of organic solvents are used in combination, the total content thereof is preferably within the above range.

In the present specification, an organic solvent means one liquid organic compound which is contained in the chemical liquid in an amount greater than 10,000 mass ppm with respect to the total mass of the chemical liquid. That is, in the present specification, a liquid organic compound contained in the chemical liquid in an amount greater than 10,000 mass ppm with respect to the total mass of the chemical liquid corresponds to an organic solvent.

In the present specification, "liquid" means that the compound stays in liquid form at 25° C. under atmospheric pressure.

The type of the organic solvents is not particularly limited, and known organic solvents can be used. Examples of the organic solvents include alkylene glycol monoalkyl ether carboxylate, alkylene glycol monoalkyl ether, a lactic acid alkyl ester, alkoxyalkyl propionate, cyclic lactone (preferably having 4 to 10 carbon atoms), a monoketone compound which may have a ring (preferably having 4 to 10 carbon atoms), alkylene carbonate, alkoxyalkyl acetate, alkyl pyruvate, and the like.

Furthermore, as the organic solvents, those described in JP2016-057614A, JP2014-219664A, JP2016-138219A, and JP2015-135379A may be used.

The organic solvent is preferably at least one kind of compound selected from the group consisting of propylene glycol monomethyl ether (PGMM), propylene glycol monoethyl ether (PGME), propylene glycol monopropyl ether (PGMP), propylene glycol monomethyl ether acetate (PGMEA), ethyl lactate (EL), methyl methoxypropionate (MPM), cyclopentanone (CyPn), cyclohexanone (CyHe), γ-butyrolactone (γBL), diisoamyl ether (DIAE), butyl acetate (nBA), isoamyl acetate (iAA), isopropanol (IPA), and 4-methyl-2-pentanol (MIBC), dimethylsulfoxide (DMSO), N-methyl-2-pyrrolidone (NMP), diethylene glycol (DEG), ethylene glycol (EG), dipropylene glycol (DPG), propylene glycol (PG), ethylene carbonate (EC), propylene carbonate (PC), sulfolane, cycloheptanone, and 2-heptanone (MAK).

The type and the content of the organic solvent in the substance to be purified can be measured using a gas chromatography mass spectrometer. The measurement condition and the like are the same as those of the method for measuring the stabilizer described above.

<Other Components>

The substance to be purified may contain other components in addition to the above components. Examples of those other components include metal impurities (metal ions and metal particles), water, and the like.

(Metal Impurities)

The substance to be purified may contain metal impurities (metal particles and metal ions).

The metal ions and the metal particles in the present specification mean metal ions and metal particles measured by Single Nano Particle Inductively Coupled Plasma Mass Spectrometry (SP-ICP-MS).

The device used in SP-ICP-MS is the same as the device used in general inductively coupled mass spectrometry (ICP-MS). The only difference between SP-ICP-MS and ICP-MS is how to analyze data. With SP-ICP-MS, data can be analyzed using commercial software.

With ICP-MS, the content of metal components as a measurement target is measured regardless of the way the metal components are present. Accordingly, the total mass of metal particles and metal ions as a measurement target is quantified as the content of metal components.

With SP-ICP-MS, the content of metal particles is measured. Accordingly, by subtracting the content of metal particles from the content of metal components in a sample, the content of metal ions in the sample can be calculated.

Examples of the device for SP-ICP-MS include Agilent 8800 triple quadrupole inductively coupled plasma mass spectrometry (ICP-MS, for semiconductor analysis, option #200) manufactured by Agilent Technologies, Inc. By using this device, the content of metal particles can be measured by the method described in Examples. In addition to the device described above, it is possible to use NexION350S manufactured by PerkinElmer Inc. and Agilent 8900 manufactured by Agilent Technologies, Inc.

Metal Ions

In a case where the substance to be purified contains metal ions, the total content of the metal ions is not particularly limited. However, in view of obtaining a chemical liquid having further improved effects of the present invention, the total content of the metal ions is preferably 1.0 to 10,000 mass ppt.

According to the examination conducted by the inventors of the present invention, it has been revealed that among metal ions, particularly, ions of Fe, Cr, Pb, and Ni (hereinafter, Fe, Cr, Pb, and Ni will be referred to as "specific metals", and ions of Fe, Cr, Pb, and Ni will be referred to as "specific metal ions" as well) easily form a complex with the decomposed product of the organic solvent described above. Furthermore, in a case where the substance to be purified contains an excess of specific metal ions, either or both of the solubility and the ion exchange rate thereof at the time of purification change, and accordingly, it is difficult to remove the metal ions. According to the examination conducted by the inventors of the present invention, provided that the substance to be purified contains one kind of specific metal ions, particularly in a case where the content of the specific metal ions with respect to the total mass of the substance to be purified is equal to or smaller than 10,000 mass ppt, a chemical liquid having further improved particle defect inhibition performance is obtained. Furthermore, provided that the substance to be purified contains two or more kinds of specific metal ions, in a case where the content of each of the specific metal ions with respect to the total mass of the substance to be purified is equal to or smaller than 10,000 mass ppt, a chemical liquid having further improved particle defect inhibition performance is obtained.

Meanwhile, in a case where the substance to be purified contains one kind of specific metal ions, and the content of the specific metal ions with respect to the total mass of the substance to be purified is equal to or greater than 1.0 mass ppt, although the detailed mechanism is unclear, at the time of filtering the substance to be purified by using a filter, surprisingly, the metal removing performance of the filter is more easily demonstrated. As a result, an unexpected effect of obtaining a chemical liquid having further improved defect inhibition performance is brought about. Furthermore, in a case where the substance to be purified contains two or more kinds of specific metal ions, and the content of each of the specific metal ions with respect to the total mass of the substance to be purified is equal to or greater than 1.0 mass ppt, although the detailed mechanism is unclear, at the time of filtering the substance to be purified by using a filter, surprisingly, the metal removing performance of the filter is more easily demonstrated. As a result, an unexpected effect of obtaining a chemical liquid having further improved defect inhibition performance is brought about.

In view of obtaining a chemical liquid having further improved effects of the present invention, in a case where the substance to be purified contains one kind of specific metal ions, the content of the specific metal ions in the substance to be purified is more preferably 1.0 to 1,500 mass ppt, and even more preferably 1.0 to 70 mass ppt. Furthermore, in a case where the substance to be purified contains two or more kinds of specific metal ions, the content of each of the specific metal ions in the substance to be purified is more preferably 1.0 to 1,500 mass ppt, and even more preferably 1.0 to 70 mass ppt.

In the present specification, metal ions mean ions of a single metal or complex ions (for example, an ammine complex, a cyano complex, a halogeno complex, a hydroxy complex, and the like).

Metal Particles

In a case where the substance to be purified contains metal particles, the total content of the metal particles is not particularly limited. However, in view of obtaining a chemical liquid having further improved effects of the present invention, the total content of the metal particles is preferably 1.0 to 10,000 mass ppt.

According to the examination conducted by the inventors of the present invention, it has been revealed that the metal particles of the specific metals (hereinafter, simply referred to as "specific metal particles" as well) particularly easily become the cause of particle defects.

That is, in a case where the substance to be purified contains one kind of specific metal particles, and the content of the specific metal particles with respect to the total mass of the substance to be purified is equal to or smaller than 10,000 mass ppt, a chemical liquid having further improved particle defect inhibition performance is obtained. Furthermore, in a case where the substance to be purified contains two or more kinds of specific metal particles, and the content of each of the specific metal particles with respect to the total mass of the substance to be purified is equal to or smaller than 10,000 mass ppt, a chemical liquid having further improved particle defect inhibition performance is obtained.

Meanwhile, in a case where the substance to be purified contains one kind of specific metal particles, and the content of the specific metal particles with respect to the total mass of the substance to be purified is equal to or greater than 1.0 mass ppt, a chemical liquid having further improved defect inhibition performance is obtained. Furthermore, in a case where the substance to be purified contains two or more kinds of specific metal particles, and the content of each of the specific metal particles with respect to the total mass of the substance to be purified is equal to or greater than 1.0 mass ppt, a chemical liquid having further improved defect inhibition performance is obtained.

Presumably, in a case where the content of the specific metal particles in the substance to be purified is equal to or greater than a predetermined value, the specific metal particles in the substance to be purified may be easily aggregated with each other due to the intermolecular interaction at the time of purification (particularly, at the time of filtration), and the apparent secondary particle diameter of the specific metal particles may increase. Presumably, as a result, the removal efficiency of the purification (particularly, filtration using a filter) may be further improved, and a chemical liquid having further improved defect inhibition performance may be obtained.

In view of obtaining a chemical liquid having further improved effects of the present invention, in a case where the substance to be purified contains one kind of specific metal particles, the content of the specific metal particles with respect to the total mass of the substance to be purified is more preferably 1.0 to 2,500 mass ppt, and even more preferably 1.0 to 800 mass ppt. In a case where the substance to be purified contains two or more kinds of specific metal particles, the content of each of the specific metal particles with respect to the total mass of the substance to be purified is more preferably 1.0 to 2,500 mass ppt, and even more preferably 1.0 to 800 mass ppt.

Water

In a case where the substance to be purified contains water, the content of the water is not particularly limited. However, in view of obtaining a chemical liquid having further improved effects of the present invention, the content of the water is preferably 500 to 50,000 mass ppm, more preferably 3,000 to 30,000 mass ppm, and even more preferably 3,000 to 15,000 mass ppm.

In a case where the content of the water in the substance to be purified is equal to or greater than 500 mass ppm, the chemical liquid has further improved stain-like defect inhibition performance. In a case where the content of the water in the substance to be purified is equal to or smaller than 50,000 mass ppm, the chemical liquid has further improved particle defect inhibition performance.

In a case where the content of water in the substance to be purified is equal to or greater than 500 mass ppt, in the substance to be purified, the stabilizer can be stably present at the time of purifying the substance to be purified. Accordingly, it is more difficult for the stabilizer from being precipitated at the time of purification (particularly, filtration), an appropriate amount of the stabilizer can be more easily retained in the substance to be purified, and consequently, it is easy to obtain a chemical liquid having further improved stain-like defect inhibition performance.

Meanwhile, in a case where the content of water in the substance to be purified is equal to or smaller than 50,000 mass ppm, it is more difficult for the metal particles to be charged, and the metal particles can be more efficiently removed at the time of purification (particularly, filtration). As a result, a chemical liquid having further improved particle defect inhibition performance is obtained.

In the present specification, the content of water in the substance to be purified refers to a content of water measured by Karl Fischer titration. The conditions for measuring the content of water in the substance to be purified by Karl Fischer titration are as described in Examples.

[Purification Step]

The chemical liquid purification method is not particularly limited. However, in view of more easily controlling the content of the stabilizer in the substance to be purified and the chemical liquid, it is preferable to use at least one kind of method selected from the group consisting of ion adsorption, ion exchange and filtration. The chemical liquid purification method more preferably includes at least one kind of method selected from the group consisting of ion adsorption, ion exchange, and filtration, and even more preferably includes only filtration.

In other words, it is preferable that the chemical liquid purification method has a purification step of purifying the substance to be purified by using at least one kind of method selected from the group consisting of ion adsorption, ion exchange, and filtration. Particularly, in view of obtaining a chemical liquid having further improved effects of the present invention, the chemical liquid purification method more preferably includes filtration. Filtration may be combined with ion adsorption or ion exchange. The chemical liquid purification method even more preferably includes only filtration.

<Filtration>

In the present specification, "filtration" means a method of purifying the substance to be purified by passing the substance to be purified through a filter. The method for passing the substance to be purified through a filter is not particularly limited. Typically, examples thereof include a method of passing the substance to be purified through a filter unit constituted with a filter cartridge having a filter and a housing accommodating the filter cartridge.

FIG. 1 is a schematic view of a typical filtering device that can be used for filtering a substance to be purified. A filtering device 10 in FIG. 1 has three units including a manufacturing tank 11 storing a substance to be purified, a filter unit 12, and a filling device 13 filling a container with a chemical liquid obtained after purification. These units are connected to each other through a pipe line 14.

The substance to be purified stored in the manufacturing tank 11 is transported to filter unit 12 by a pump not shown in the drawing, filtered through the filter included in the filter cartridge accommodated in the filter unit 12, and stored in a container by the filling device 13.

Although the filtering device 10 has one filter unit, the device performing the purification method described above is not limited thereto and may have two or more independent filter units in the pipe line. In a case where the filtering device has two or more independent filter units, the arrangement of the filter units is not particularly limited. Two or more of the filter units may be arranged in series or in parallel.

The filtering device 10 has a constitution in which the substance to be purified filtered through the filter unit 12 is transported to the filling device 13 and stored in a container (the flow of the substance to be purified is indicated by $F_O$ in FIG. 1). However, the device performing the purification method described above is not limited thereto, and may have a constitution in which the substance to be purified filtered through the filter unit 12 is sent back to the manufacturing tank 11 such that the substance to be purified passes again through the filter unit 12. In a case where the substance to be purified filtered through the filter unit 12 is sent back to the manufacturing tank 11 and passed again through the filter unit 12, the amount of metal impurities and the like contained in the chemical liquid can be further reduced. This filtration method is called circulation filtration.

Figure 2:
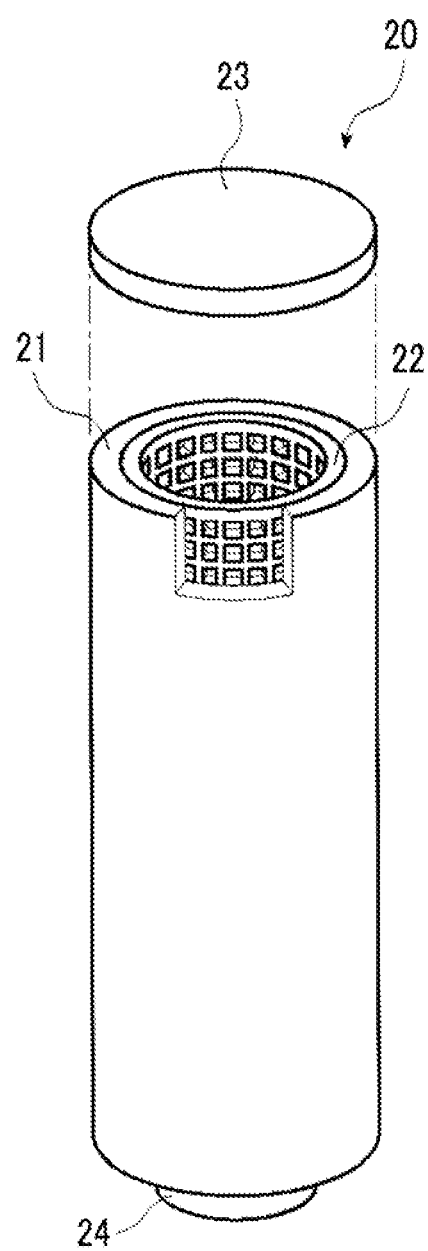
FIG. 2 is a partially exploded perspective view of a typical filter cartridge accommodated in a filter unit.

FIG. 2 is a partially exploded perspective view of a typical filter cartridge accommodated in a filter unit 12. A filter cartridge 20 has a cylindrical filter 21, and a cylindrical core 22 for supporting the filter 21 so as to contact the inside of the filter 21. The cylindrical core 22 is in the form of a mesh, and a liquid can easily pass through the mesh. On top of the filter 21 and the core 22, a cap 23 is disposed so as to cover the upper end portion of the members. Furthermore, on bottom of the members, a liquid inlet 24 for allowing a substance to be purified to flow into the core 22 is disposed. Furthermore, on the outside of the filter 21, a protector may be disposed which is constituted to enable a liquid to easily pass and protects the filter 21.

Figure 3:
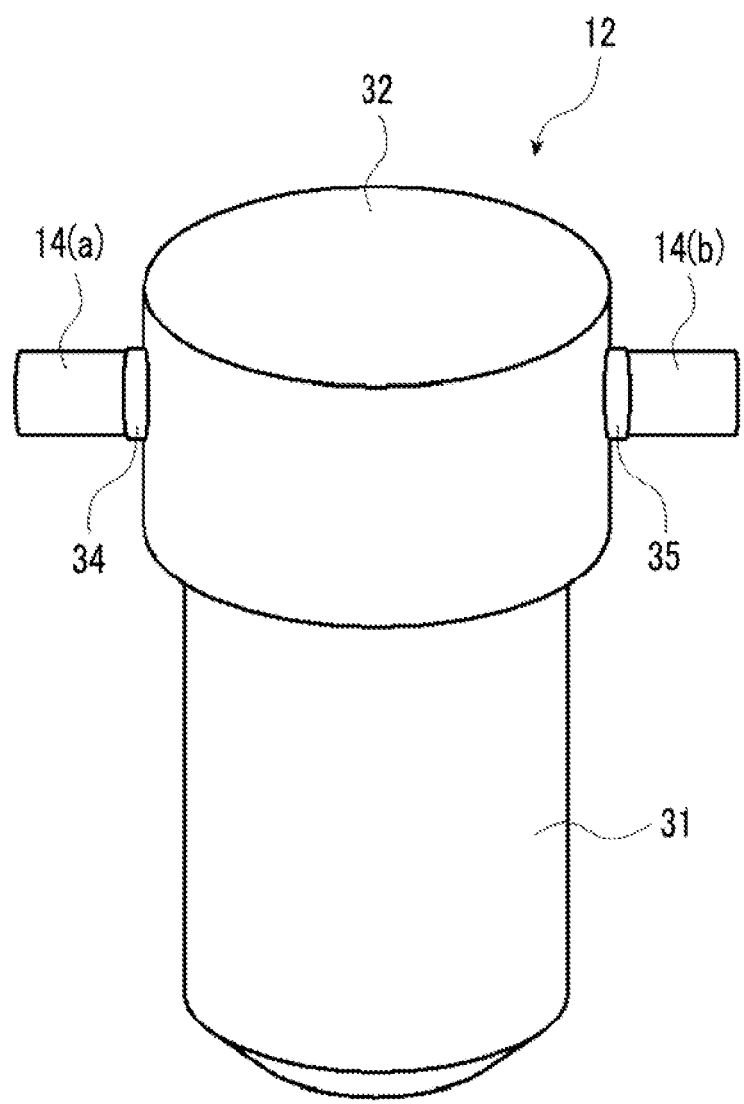
FIG. 3 is a perspective view of a filter unit.

FIG. 3 is a perspective view of the filter unit 12. The filter unit 12 has a housing, which is constituted with a body 31 and a lid 32, and a filter cartridge not shown in the drawing that is accommodated in the housing. On the lid 32, a liquid inlet 34 to be connected to a pipe line 14(a) and a liquid outlet 35 to be connected to the pipe line 14(b) are disposed.

The filter unit 12 shown in FIG. 3 has the liquid inlet 34 and the liquid outlet 35 on the lid 32. However, the filter unit is not limited thereto, and the liquid inlet and the liquid outlet can be disposed at any place of the lid 32 and/or the body 31. Furthermore, although the filter unit 12 shown in FIG. 3 has the body 31 and the lid 32, the body and the lid may be constituted as an integral unit.

Figure 4:
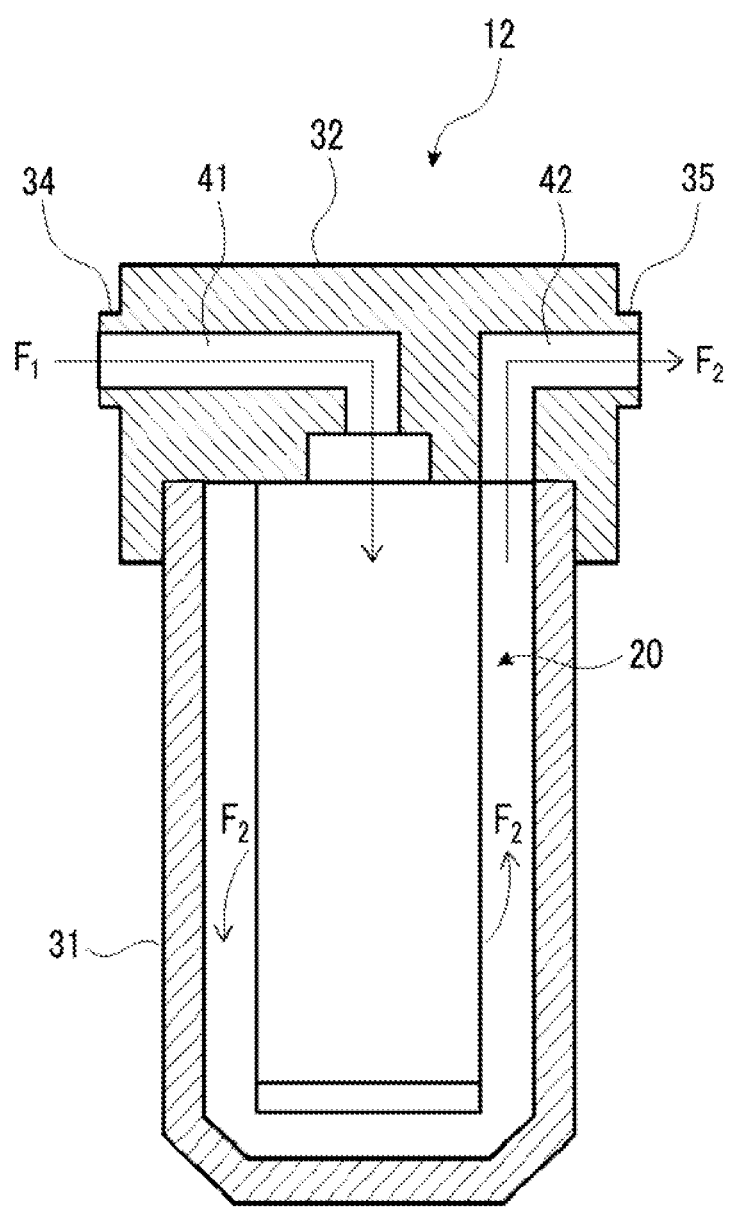
FIG. 4 is a partial cross-sectional view of the filter unit.

FIG. 4 is a partial cross-sectional view of the filter unit 12. The filter unit 12 comprises the liquid inlet 34 and the liquid outlet 35 on the lid 32. The liquid inlet 34 is connected to an internal pipe line 41, and the liquid outlet 35 is connected to an internal pipe line 42. The flow of a substance to be purified is indicated by $F_1$. The substance to be purified having flown into the filter unit from the liquid inlet 34 flows into the body 31 through the internal pipe line 41 provided in the interior of the lid 32, passes through the filter from the core of the filter cartridge 20, and flows into the outer surface. In this process, the substance to be purified is purified.

The purified substance to be purified having flown out to the outer surface passes through the internal pipe line 42 and taken out of the liquid outlet 35 (along the flow indicated by $F_2$ in FIG. 4).

<Filter>

The pore size of the filters is not particularly limited as long as it is generally used for filtering a substance to be purified. Especially, in view of obtaining a chemical liquid having further improved effects of the present invention, the pore size of the filters is preferably equal to or greater than 1.0 nm and equal to or smaller than 1.0 μm. In the present specification, the pore size of a filter means a pore size determined by the bubble point of isopropanol (IPA) or HFE-7200 ("NOVEC 7200", manufactured by 3M Company, hydrofluoroether, $C_4F_9OC_2H_5$).

The material of the filters is not particularly limited. In a case where the material is a resin, examples of the resin include polyfluorocarbon such as polytetrafluoroethylene and perfluoroalkoxyalkane; polyamide such as nylon 6 and nylon 66; polyimide; polyamide imide; polyester; a polyolefin (including a high density polyolefin and an ultra-high-molecular-weight polyolefin) such as polyethylene and polypropylene (PP); polyether sulfone; cellulose; and the like.

Furthermore, in addition to a resin, diatomite, glass, and the like may also be used.

A surface treatment may be performed on the filters. As the surface treatment method, known methods can be used without particular limitation. Examples of the surface treatment method include a chemical modification treatment, a plasma treatment, a hydrophobization treatment, coating, a gas treatment, sintering, and the like.

The pore structure of the filters is not particularly limited, and may be appropriately selected according to the form of impurities contained in a substance to be purified. The pore structure of the filters means the pore size distribution, the positional distribution of pores in the filters, the shape of pores, and the like. Typically, the pore structure varies with the method for manufacturing the filters.

For example, the pore structure varies between a porous membrane formed by sintering powder of a resin or the like and a fibrous membrane formed by methods such as electrospinning, electroblowing, and melt blowing.

The critical surface tension of the filter is not particularly limited, and can be appropriately selected according to the impurities that should be removed. For example, in view of efficiently removing impurities with high polarity and metal impurities, the critical surface tension is preferably equal to or higher than 70 mN/m and equal to or lower than 95 mN/m. The critical surface tension of the filters is more preferably 75 to 85 mN/m. The value of the critical surface tension is a nominal value from the manufacturer.

The temperature at which a substance to be purified passes through the filters is not particularly limited, but is preferably less than room temperature in general.

There is no particular limitation on the value of a distance (Ra) between a substance to be purified and the material of each filter in the Hansen space and on the value of a radius of an interaction sphere, that is, the value of an interaction radius (R0) of the material of each filter. However, in view of reducing the amount of impurities derived from each filter that are eluted into the substance to be purified, it is preferable to control Ra and R0. That is, in a relationship among Hansen solubility parameters $\delta_{Dp}$, $\delta_{Pp}$, and $\delta_{Hp}$ and an interaction radius R0 of each filter and Hansen solubility parameters $\delta_{Ds}$, $\delta_{Ps}$, and $\delta_{Hs}$ of the substance to be purified, provided that Ra is represented by an equation of $Ra^2 = 4(\delta Ds - \delta Dp)^2 + (\delta Ps - \delta Pp)^2 + (\delta Hs - \delta Hp)^2$, a ratio of Ra to R0 is preferably equal to or lower than 1.0.

The filtering speed is not particularly limited. However, in view of obtaining a chemical liquid having further improved effects of the present invention, the filtering speed is preferably equal to or higher than 1.0 L/min/m$^2$, more preferably equal to or higher than 0.75 L/min/m$^2$, and even more preferably equal to or higher than 0.6 L/min/m$^2$.

For the filter, an endurable differential pressure for assuring the filter performance (assuring that the filter will not be broken) is set. In a case where the endurable differential pressure is high, by increasing the filtering pressure, the filtering speed can be increased. That is, it is preferable that the upper limit of the filtering speed is generally equal to or lower than 10.0 L/min/m$^2$ although the upper limit usually depends on the endurable differential pressure of the filter.

In the chemical liquid purification method described above, in view of obtaining a chemical liquid having further improved defect inhibition performance, the filtering pressure is preferably 0.001 to 1.0 MPa, more preferably 0.003 to 0.5 MPa, and even more preferably 0.005 to 0.3 MPa.

Particularly, in a case where a filter having a small pore size is used, by increasing the filtering pressure, the amount of impurities as particles in the substance to be purified can be more efficiently reduced. In a case where a filter having a pore size smaller than 20 nm is used, the filtering pressure is preferably 0.005 to 0.3 MPa.

The filtering pressure affects the filtering accuracy. Therefore, it is preferable that the pulsation of pressure at the time of filtering is as low as possible.

The smaller the pore size of a filter, the lower the filtering speed. However, in a case where a plurality of filters of the same type are connected to each other in parallel, the filtration area is enlarged, and the filtering pressure is reduced. In this way, the reduction of the filtering speed can be compensated.

In a case where a substance to be purified is filtered using a plurality of filters, the pore size, the material, and the pore structure of the filters may be the same as each other. However, in a case where a plurality of filters, which are different from each other in terms of at least one kind of item selected from the group consisting of the pore size, the material, and the pore structure of the filters, are used in combination, it is possible to more effectively remove impurities in the substance to be purified.

In a case where the filtering device has a plurality of filter units, and the filter units are arranged in series in the pipe line, it is preferable that the filters included in the filter units are formed of a hydrophilic material and a hydrophobic material. In the present specification, a hydrophilic material means a material by which the water contact angle on the surface of the filter becomes equal to or greater than 450 at 25° C., and a hydrophobic material means a material by which the water contact angle on the surface of the filter becomes less than 45° at 25° C.

The filter formed of a hydrophilic material (hereinafter, referred to as "hydrophilic filter" as well) can efficiently remove metal impurities contained in a substance to be purified. In a case where such a filter is disposed at the end of the pipe line, that is, in a case where the substance to be purified is caused to finally pass through a hydrophilic filter, a chemical liquid with a reduced metal impurity content is obtained.

In a case where a plurality of filter units are used by being arranged in series in the pipe line, a differential pressure before and after a substance to be purified passes through each of the filter units is preferably equal to or higher than 50 kPa and equal to or lower than 250 kPa. In a case where the differential pressure is controlled within the above range, it is possible to prevent impurities from being eluted into the substance to be purified from the filters.

It is preferable to wash the filters by using a washing solution before purifying a substance to be purified. In a case where the filters are washed before the substance to be purified is used, it is possible to prevent impurities having adhered to the filters from migrating to the substance to be purified.

The washing solution is not particularly limited, and examples thereof include the organic solvent described above, the chemical liquid which will be described later, a solution obtained by diluting the chemical liquid, and the like.

The method for washing the filters is not particularly limited, and examples thereof include a method of passing the aforementioned washing solution through the filters set in the housing, a method of immersing the filters in the washing solution on the outside of the filtering device, and the like. In view of further inhibiting the mixing of impurities into the filtering device, it is preferable to use the method of immersing the filters in the washing solution on the outside of the filtering device.

In a case where a plurality of filter units are used by being arranged in series in the pipe line, the material and the pore structure of the filters are not particularly limited. At least one of the filters preferably contains nylon, and is more preferably formed of nylon.

The pore structure of the filter containing nylon is not particularly limited. However, it is preferable that the filter is a fibrous membrane.

From the viewpoint of efficiently removing metal particles and the like in a substance to be purified, it is preferable to use a filter having a pore size equal to or smaller than 20 nm. Particularly, in view of obtaining a chemical liquid having further improved effects of the present invention, the pore size is preferably 1.0 to 15 nm, and more preferably 1.0 to 12 nm. In a case where the pore size is equal to or smaller than 15 nm, a target substance can be more thoroughly removed. In a case where the pore size is equal to or greater than 1.0 nm, the filtering efficiency is further improved.

In a case where a plurality of filter units are arranged in series in the pipe line, and a substance to be purified contains a colloidalized target substance, it is preferable to dispose a filter having a larger pore size on a primary side of the filter for removing metal particles and the like described above.

For example, in a case where microfiltration filter having a pore size equal to or smaller than 20 nm is used for removing metal particles, by disposing a filter having a pore size equal to or greater than 50 nm on the primary side thereof, it is possible to further improve the filtering efficiency and to more thoroughly remove a particle-like target substance.

From the viewpoint of efficiently removing metal ions and the like in a substance to be purified, it is preferable to use a metal ion adsorption filter. The material of the metal ion adsorption filter is not particularly limited, but it is preferable that the material has acid groups such as a sulfo group and a carboxy group on the surface thereof.

Examples of materials of the metal ion adsorption filter include cellulose, diatomite, nylon, polyethylene, polypropylene, polystyrene, a fluorine-containing resin, and the like.

The metal ion adsorption filter may be constituted with a material containing polyimide and/or polyamide imide. Examples of the metal ion adsorption filter include the polyimide and/or polyamide imide porous membrane described in JP2016-155121A.

The polyimide and/or polyamide imide porous membrane may contain at least one group selected from the group consisting of a carboxy group, a salt-type carboxy group, and a —NH— bond. In a case where the metal ion adsorption filter is formed of a fluorine-containing resin, polyimide, and/or polyamide imide, the filter has further improved solvent resistance.

From the viewpoint of efficiently removing organic impurities in a substance to be purified and from the viewpoint of easily controlling the content of the stabilizer contained a substance to be purified within a predetermined range, it is preferable that the filter has the skeleton of an organic substance, which can interact with the organic impurities, on the surface thereof (in other words, it is preferable that the surface of the filter is modified with the skeleton of an organic substance which can interact with the organic impurities). Examples of the skeleton of an organic substance which can interact with the organic impurities include a chemical structure which can react with the organic impurities so as to make the organic impurities entrapped in an organic impurity adsorption filter. More specifically, in a case where the substance to be purified contains long-chain n-alkyl alcohol (structural isomer in a case where long-chain 1-alkyl alcohol is used as an organic solvent) as organic impurities, examples of the skeleton of an organic substance include an alkyl group. Furthermore, in a case where the substance to be purified includes include dibutylhydroxytoluene (BHT) as organic impurities, examples of the skeleton of an organic substance include a phenyl group.

Examples of the base material (material) constituting the organic impurity adsorption filter include cellulose supporting active carbon, diatomite, nylon, polyethylene, polypropylene, polystyrene, a fluorine-containing resin, and the like.

Furthermore, as the organic impurity adsorption filter, it is possible to use the filters obtained by fixing active carbon to non-woven cloth that are described in JP2002-273123A and JP2013-150979A.

For the organic impurity adsorption filter, in addition to the chemical adsorption described above (adsorption using an organic impurity removing filter having the skeleton of an organic substance, which can interact with organic impurities, on the surface thereof), a physical adsorption method can also be used.

For example, in a case where the substance to be purified contains BHT as organic impurities, the structure of BHT is larger than 1.0 nm. Accordingly, in a case where an organic impurity adsorption filter having a pore size of 1.0 nm is used, BHT cannot pass through the pore of the filter. That is, by being physically entrapped by the filter, BHT is removed from the substance to be purified. In this way, for removing organic impurities, not only chemical interaction but also a physical removing method can be used.

<Ion Exchange>

In the present specification, ion exchange means a method for removing metal ions and the like contained in a substance to be purified without using a filter.

Typical examples of the ion exchange include a method of passing a substance to be purified through an ion exchange unit. The method of passing a substance to be purified through the ion exchange unit is not particularly limited, and examples thereof include a method of disposing an ion exchange unit in the filtering device 10 described above instead of the filter unit 12 or in the pipe line on the primary side or the secondary side of the filter unit 12 and passing a substance to be purified through the ion exchange unit under pressure or without applying pressure.

As the ion exchange unit, known ion exchange units can be used without particular limitation. Examples of the ion exchange unit include a tower-like container (resin tower) storing an ion exchange resin, an electrodialysis device using an ion exchange membrane, and the like.

In a case where an ion exchange resin is used, a cation exchange resin or an anion exchange resin may be used as a single bed, a cation exchange resin and an anion exchange resin may be used as a dual bed, or a cation exchange resin and an anion exchange resin may be used as a mixed bed.

In order to reduce the amount of moisture eluted from the ion exchange resin, as the ion exchange resin, it is preferable to use a dry resin which does not contain moisture as far as possible. As the dry resin, commercial products can be used, and examples thereof include 15JS-HG-DRY (trade name, dry cation exchange resin, moisture content: equal to or smaller than 2%) and MSPS2-1-DRY (trade name, mixed bed resin, moisture content: equal to or smaller than 10%) manufactured by ORGANO CORPORATION, and the like.

In a case where an electrodialysis device using an ion exchange membrane is used, the substance to be purified can be treated at a high flow rate. The ion exchange membrane is not particularly limited, and examples thereof include NEOSEPTA (trade name, manufactured by ASTOM Corporation), and the like.

<Ion Adsorption>

In the present specification, ion adsorption means a method for removing metal ions and the like contained in a substance to be purified without using a filter.

Typically, examples of the ion adsorption include a method of using, instead of the ion exchange resin described above, an ion adsorption resin and/or a chelating agent having a function of entrapping metal ions in a substance to be purified. As the chelating agent, for example, it is possible to use the chelating agents described in JP2016-028021A, JP2000-169828A, and the like. Furthermore, as the ion adsorption resin, for example, it is possible to use the ion adsorption resins described in JP2001-123381A, JP2000-328449A, and the like.

[Other Steps]

The chemical liquid purification method may have other steps in addition to the above. Examples of those other steps include a moisture content-adjusting step, an electricity removing step, and the like.

<Moisture Content-Adjusting Step>

The moisture content-adjusting step is a step of adjusting the content of water in a substance to be purified. The method for adjusting the content of water is not particularly limited, and examples thereof include a method of adding water to the substance to be purified and a method of removing water in the substance to be purified.

As the method for removing water, known dehydration methods can be used without particular limitation.

Examples of the method for removing water include a dehydration membrane, a water adsorbent insoluble in an organic solvent, an aeration purge device using a dry inert gas, a heating or vacuum heating device, and the like.

In a case where the dehydration membrane is used, dehydration is performed using the membrane by means of pervaporation (PV) or vapor permeation (VP). The dehydration membrane is constituted, for example, as a permeable membrane module. As the dehydration membrane, it is possible to use membranes formed of a polymer-based material such as polyimide-based material, a cellulose-based material, or a polyvinyl alcohol-based material or an inorganic material such as zeolite.

The water adsorbent is used by being added to a substance to be purified. Examples of the water adsorbent include zeolite, diphosphorus pentoxide, silica gel, calcium chloride, sodium sulfate, magnesium sulfate, anhydrous zinc chloride, fuming sulfuric acid, soda lime, and the like.

In a case where zeolite (particularly, MOLECULAR SIEVE (trade name) manufactured by Union Showa K.K.) is used for the dehydration treatment, olefins can also be removed.

<Electricity Removing Step>

The electricity removing step is a step of removing electricity from a substance to be purified such that the charge potential thereof is reduced.

As the electricity removing method, known electricity removing methods can be used without particular limitation. Examples of the electricity removing method include a method of bringing the substance to be purified into contact with a conductive material.

The contact time for which the substance to be purified is brought into contact with a conductive material is preferably 0.001 to 60 seconds, more preferably 0.001 to 1 second, and even more preferably 0.01 to 0.1 seconds. Examples of the conductive material include stainless steel, gold, platinum, diamond, glassy carbon, and the like.

Examples of the method for bringing the substance to be purified into contact with a conductive material include a method of disposing a grounded mesh formed of a conductive material in the interior of a pipe line and passing the substance to be purified through the mesh, and the like.

Each of the steps described above is preferably performed under a sealed condition in an inert gas atmosphere in which water is less likely to be mixed into the substance to be purified.

Furthermore, in order to inhibit the intermixing of moisture as much as possible, each of the steps is preferably performed in an inert gas atmosphere in which a dew-point temperature is equal to or lower than −70° C. This is because in the inert gas atmosphere at a temperature equal to or lower than −70° C., the concentration of moisture in a gas phase is equal to or lower than 2 mass ppm, and hence the likelihood that moisture will be mixed into the substance to be purified is reduced.

The chemical liquid purification method may have, for example, a step of performing an adsorption and purification treatment on metal components by using silicon carbide described in WO2012/043496A, in addition to the steps described above.

The chemical liquid purification method may have a step of distilling a substance to be purified. In the purification step, the substance to be purified contains a predetermined amount of stabilizer, and the chemical liquid also contains a predetermined amount of stabilizer. In other words, in view of easily controlling the content of the stabilizer in the entire step, it is preferable that the chemical liquid purification method does not include a distillation step. In a case where the chemical liquid purification method has a distillation step, the stabilizer may be added as needed to the distilled substance to be purified.

In a case where the chemical liquid is purified using the filtering device illustrated in FIG. 1 or using a device obtained by adding other units (for example, a distillation column and/or a resin column) to the filtering device illustrated in FIG. 1, as the material of a liquid contact portion of the filtering device, known materials can be used without particular limitation. Particularly, in view of obtaining a chemical liquid having further improved effects of the present invention, it is preferable that the liquid contact portion of the filtering device and the like is formed of a nonmetallic material or an electropolished metallic material which will be described later.

The liquid contact portion of the filtering device and the like means a portion in each unit (the manufacturing tank, the filter unit, the filtering device, or the like), the pipe line, the pump included in these, and the like that is likely to contact the substance to be purified or the chemical liquid.

During the purification of a chemical liquid, it is preferable that all of the opening of a container, washing of a container and a device, storage of a solution, analysis, and the like that are included in the purification are performed in a clean room. It is preferable that the clean room meets the 14644-1 clean room standard. The clean room preferably meets any of International Organization for Standardization (ISO) class 1, ISO class 2, ISO class 3, or ISO class 4, more preferably meets ISO class 1 or ISO class 2, and even more preferably meets ISO class 1.

[Chemical Liquid]

It is preferable that the chemical liquid purified by the above purification method is used for manufacturing semiconductor devices. Specifically, it is preferable that the chemical liquid is used for treating organic substances and the like in a wiring forming process (including a lithography step, an etching step, an ion implantation step, a peeling step, and the like) including photolithography. More specifically, the chemical liquid is preferably used as a prewet solution, a developer, a rinsing solution, a peeling solution, a CMP slurry, a washing solution used after CMP (p-CMP rinsing solution), and the like.

The rinsing solution can be used for rinsing the edge line of a wafer before and after being coated with a resist solution.

Furthermore, the chemical liquid can be used as a diluent for a resin contained in a composition for forming a resist film (resist composition) used for manufacturing semiconductor devices. That is, the chemical liquid can be used as a solvent for the composition for forming a resist film.

In addition, the chemical liquid may be used by being diluted with another organic solvent and/or water, and the like.

In a case where the chemical liquid is used as a CMP slurry, for example, abrasive grains, an oxidant, and the like may be added to the chemical liquid. Moreover, the chemical liquid can also be used as a solvent for diluting a CMP slurry.

The chemical liquid can be suitably used for other purposes in addition to the manufacturing of semiconductor devices. The chemical liquid can be used as a developer for polyimide, a resist for sensor, and a resist for lens, a rinsing solution, and the like.

In addition, the chemical liquid can also be used as a solvent for medical uses or for washing. Particularly, the chemical liquid can be suitably used for washing containers, piping, substrates (for example, a wafer and glass), and the like.

[Suitable Aspects of Chemical Liquid]

Hereinafter, a suitable aspect of the chemical liquid according to the embodiment of the present invention will be described, but the chemical liquid according to the embodiment of the present invention is not limited thereto.

The suitable aspect of the chemical liquid according to the embodiment of the present invention is a chemical liquid containing an organic solvent, a stabilizer, specific metal ions, and specific metal particles.

In the chemical liquid according to the present embodiment, the content of the stabilizer with respect to the total mass of the chemical liquid is 0.1 to 50 mass ppm.

In a case where the chemical liquid according to the present embodiment contains one kind of specific metal ions, the content of the specific metal ions with respect to the total mass of the chemical liquid is equal to or smaller than 100 mass ppt. In a case where the chemical liquid contains two or more kinds of specific metal ions, the content of each of the specific metal ions with respect to the total mass of the chemical liquid is equal to or smaller than 100 mass ppt. In a case where the chemical liquid contains one kind of specific metal particles, the content of the specific metal particles with respect to the total mass of the chemical liquid is equal to or smaller than 100 mass ppt. In a case where the chemical liquid contains two or more kinds of specific metal particles, the content of each of the specific metal particles with respect to the total mass of the chemical liquid is equal to or smaller than 100 mass ppt.

<Organic Solvent>

The chemical liquid contains an organic solvent. The content of the organic solvent in the chemical liquid is not particularly limited. Generally, the content of the organic solvent with respect to the total mass of the chemical liquid is preferably equal to or greater than 99.0% by mass, more preferably equal to or greater than 99.9% by mass, even more preferably equal to or greater than 99.99% by mass, particularly preferably equal to or greater than 99.999% by mass, and most preferably equal to or greater than 99.9998% by mass. One kind of organic solvent may be used singly, or two or more kinds of organic solvents may be used in combination. In a case where two or more kinds of organic solvents are used in combination, the total content thereof is preferably within the above range.

The aspect of the organic solvent is the same as that described above as the organic solvent contained in a substance to be purified.

<Stabilizer>

The chemical liquid contains a stabilizer. In the chemical liquid, the content of the stabilizer with respect to the total mass of the chemical liquid is 0.1 to 50 mass ppm.

The aspect of the stabilizer is the same as that of the aforementioned stabilizer contained in the substance to be purified.

<Metal Impurities>

The chemical liquid contains metal impurities. The total content of the metal impurities in the chemical liquid is not particularly limited. However, in view of obtaining a chemical liquid having further improved effects of the present invention, the total content of the metal impurities is preferably 0.01 to 50 mass ppt. The total content described above means the total content of metal ions and metal particles.

Particularly, in view of obtaining a chemical liquid having further improved effects of the present invention, the total content of the specific metal is preferably 0.01 to 30 mass ppt.

(Specific Metal Ion)

The chemical liquid contains specific metal ions. In a case where the chemical liquid contains one kind of specific metal ions, the content of the specific metal ions with respect to the total mass of the chemical liquid is equal to or smaller than 100 mass ppt. In a case where the chemical liquid contains two or more kinds of specific metal ions, the content of each of the specific metal ions with respect to the total mass of the chemical liquid is equal to or smaller than 100 mass ppt. The lower limit of the content of the specific metal ions in the chemical liquid is not particularly limited, but is equal to or greater than 0.1 mass ppt in many cases.

(Specific Metal Particles)

The chemical liquid contains specific metal particles. In a case where the chemical liquid contains one kind of specific metal particles, the content of the specific metal particles with respect to the total mass of the chemical liquid is equal to or smaller than 100 mass ppt. In a case where the chemical liquid contains two or more kinds of specific metal particles, the content of each of the specific metal particles with respect to the total mass of the chemical liquid is equal to or smaller than 100 mass ppt. The lower limit of the content of the specific metal particles in the chemical liquid is not particularly limited, but is equal to or greater than 0.1 mass ppt in many cases.

<Container>

The chemical liquid may be temporarily stored in a container until the chemical liquid is used. As the container for storing the chemical liquid, known containers can be used without particular limitation.

As the container storing the chemical liquid, a container for manufacturing semiconductor devices is preferable which has high internal cleanliness and hardly causes elution of impurities.

Examples of the usable container specifically include a "CLEAN BOTTLE" series manufactured by AICELLO CORPORATION, "PURE BOTTLE" manufactured by KODAMA PLASTICS Co., Ltd., and the like, but the container is not limited to these.

As the container, for the purpose of preventing mixing of impurities into the chemical liquid (contamination), it is also preferable to use a multilayer bottle in which the inner wall of the container has a 6-layer structure formed of 6 kinds of resins or a multilayer bottle having a 7-layer structure formed of 6 kinds of resins. Examples of these containers include the containers described in JP2015-123351A.

It is preferable that a liquid contact portion of the container is formed of a nonmetallic material or an elecltropolished metallic material.

As the nonmetallic material, for example, a polyethylene resin, a polypropylene resin, a polyethylene-polypropylene resin, or a fluorine-containing resin such as a fluorine-containing resin is preferable, and a fluorine-containing resin is more preferable because few metal atoms are eluted from this material.

Examples of the fluorine-containing resin include polytetrafluoroethylene (PTFE), a tetrafluoroethylene-perfluoroalkyl vinyl ether copolymer (PFA), a polytetrafluoroethylene-hexafluoropropylene copolymer resin (FEP), a polytetrafluoroethylene-ethylene copolymer resin (ETFE), a chlorotrifluoroethylene-ethylene copolymer resin (ECTFE), a vinylidene fluoride resin (PVDF), a chlorotrifluoroethylene copolymer resin (PCTFE), a vinyl fluoride resin (PVF), and the like.

As the fluorine-containing resin, polytetrafluoroethylene, a tetrafluoroethylene-perfluoroalkyl vinyl ether copolymer, or a polytetrafluoroethylene-hexafluoropropylene copolymer resin is preferable.

In a case where a container in which the liquid contact portion is formed of polyfluorocarbon is used, the occurrence of a problem such as elution of an ethylene or propylene oligomer can be further inhibited than in a case where a container, in which the liquid contact portion is formed of a polyethylene resin, a polypropylene resin, or a polyethylene-polypropylene resin, is used.

Specific examples of the container in which the liquid contact portion is formed of polyfluorocarbon include FluoroPure PFA composite drum manufactured by Entegris, Inc., and the like. Furthermore, it is possible to use the containers described on p. 4 in JP1991-502677A (JP-H03-502677A), p. 3 in WO2004/016526A, p. 9 and p. 16 in WO99/046309A, and the like. In a case where the nonmetallic material is used for the liquid contact portion, it is preferable to inhibit the elution of the nonmetallic material into the chemical liquid.

As the metallic material, known materials can be used without particular limitation.

Examples of the metallic material include a metallic material in which the total content of chromium and nickel with respect to the total mass of the metallic material is greater than 25% by mass. The total content of chromium and nickel is more preferably equal to or greater than 30% by mass. The upper limit of the total content of chromium and nickel in the metallic material is not particularly limited, but is preferably equal to or smaller than 90% by mass in general.

Examples of the metallic material include stainless steel, carbon steel, alloy steel, nickel-chromium-molybdenum steel, chromium steel, chromium-molybdenum steel, manganese steel, a nickel-chromium alloy, and the like.

As the stainless steel, known stainless steel can be used without particular limitation. Among these, an alloy with a nickel content equal to or higher than 8% by mass is preferable, and austenite-based stainless steel with a nickel content equal to or higher than 8% by mass is more preferable. Examples of the austenite-based stainless steel include Steel Use Stainless (SUS) 304 (Ni content: 8% by mass, Cr content: 18% by mass), SUS304L (Ni content: 9% by mass, Cr content: 18% by mass), SUS316 (Ni content: 10% by mass, Cr content: 16% by mass), SUS316L (Ni content: 12% by mass, Cr content: 16% by mass), and the like.

As the nickel-chromium alloy, known nickel-chromium alloys can be used without particular limitation. Among these, a nickel-chromium alloy is preferable in which the nickel content is 40% to 75% by mass and the chromium content is 1% to 30% by mass with respect to the total mass of the metallic material.

Examples of the nickel-chromium alloy include HASTELLOY (trade name, the same is true for the following description), MONEL (trade name, the same is true for the following description), INCONEL (trade name, the same is true for the following description), and the like. More specifically, examples thereof include HASTELLOY C-276 (Ni content: 63% by mass, Cr content: 16% by mass), HASTELLOY C (Ni content: 60% by mass, Cr content: 17% by mass), HASTELLOY C-22 (Ni content: 61% by mass, Cr content: 22% by mass), and the like.

Furthermore, if necessary, the nickel-chromium alloy may further contain boron, silicon, tungsten, molybdenum, copper, cobalt, and the like in addition to the aforementioned alloy.

As the method for electropolishing the metallic material, known methods can be used without particular limitation. For example, it is possible to use the methods described in paragraphs "0011" to "0014" in JP2015-227501A, paragraphs "0036" to "0042" in JP2008-264929A, and the like.

Presumably, in a case where the metallic material is electropolished, the chromium content in a passive layer on the surface thereof may become higher than the chromium content in the parent phase. Presumably, for this reason, in a case where the liquid contact portion is formed of an electropolished metallic material, the metal impurities containing metal atoms may not easily flow into the substance to be purified, and hence a chemical liquid with a reduced impurity content can be obtained.

The metallic material may have undergone buffing. As the buffing method, known methods can be used without particular limitation. The size of abrasive grains used for finishing the buffing is not particularly limited, but is preferably equal to or smaller than #400 because such grains make it easy to further reduce the surface asperity of the metallic material. The buffing is preferably performed before the electropolishing.

The content mass ratio of a content of Cr to a content of Fe (hereinafter, referred to as "Cr/Fe" as well) in the stainless steel forming the liquid contact portion of the container is not particularly limited. Generally, Cr/Fe is preferably 0.5 to 4. Particularly, in view of making it more difficult for the impurity metals and/or the organic impurities to be eluted into the chemical liquid that will be stored in the container, Cr/Fe is more preferably higher than 0.5 and lower than 3.5. In a case where Cr/Fe is higher than 0.5, the elution of a metal from the interior of the container can be inhibited. In a case where Cr/Fe is lower than 3.5, the exfoliation of the inner container that causes particles and the like do not easily occur.

The method for adjusting Cr/Fe in the stainless steel is not particularly limited, and examples thereof include a method of adjusting the content of Cr atoms in the stainless steel, a method of performing electropolishing such that the content of chromium in a passive layer on a polished surface becomes greater than the content of chromium in the parent phase, and the like.

It is preferable that the interior of the aforementioned container is washed before the solution is stored into the container. As a liquid used for washing, the washing solution described above, the chemical liquid itself, or a liquid obtained by diluting the chemical liquid is preferable. After being manufactured, the chemical liquid may be bottled using a container such as a gallon bottle or a quart bottle, transported, and stored. The gallon bottle may be formed of a glass material or other materials.

In order to prevent the change of the components in the solution during storage, purging may be performed in the interior of the container by using an inert gas (nitrogen, argon, or the like) having a purity equal to or higher than 99.99995% by volume. Particularly, a gas with small moisture content is preferable. The temperature at the time of transport and storage may be room temperature. However, in order to prevent alteration, the temperature may be controlled within a range of −20° C. to 30° C.

EXAMPLES

Hereinafter, the present invention will be more specifically described based on examples. The materials, the amount and proportion of the materials used, the details of treatments, the procedure of treatments, and the like shown in the following examples can be appropriately modified as long as the gist of the present invention is maintained. Accordingly, the scope of the present invention is not limited to the following examples.

Regarding the measurement of various components, in a case where the amount of a component as a measurement target is outside the range that can be measured using each measurement device (for example, in a case where the amount of a component is equal to or smaller than the measurement limit), the measurement target is measured after being concentrated or diluted using a glass tool thoroughly washed with the measurement target (a substance to be purified or a chemical liquid).

Example 1

Commercial PGMM (1 L) was prepared and distilled such that a stabilizer was removed. Butylhydroxytoluene (BHT, corresponding to a stabilizer, 3.0 mass ppm) was added to the distilled PGMM, thereby obtaining a substance to be purified. For the substance to be purified, the content of an organic solvent, a stabilizer, water, and metal impurities was measured by the method which will be described later. Table 1 shows the type and the content of the organic solvent, the type and the content of the stabilizer, the content of moisture, and the content of the metal impurities by type.

Furthermore, the substance to be purified was purified by the method which will be described later, thereby obtaining a chemical liquid. The content of the metal impurities in the chemical liquid by type was measured by the same method as that described above, and shown in Table 1. In addition, the defect inhibition performance of the chemical liquid was measured by the method which will be described later. The results are shown in Table 1.

Examples 1 to 51 and Comparative Examples 1 and 2

Chemical liquids were obtained in the same manner as in Example 1, except that commercial organic solvents (or a mixture thereof) described in Table 1 were used instead of PGMM, the stabilizer described in Table 1 was added in the amount described in Table 1 instead of 3.0 mass ppm of BHT, and the substance to be purified was purified by the purification method described in 1. The defect inhibition performance of the chemical liquids was evaluated. The results are shown in Table 1.

The abbreviations in Table 1 represent the following organic solvents or stabilizers.

PGMM: propylene glycol monomethyl ether
PGME: propylene glycol monoethyl ether
PGMP: propylene glycol monopropyl ether
PGMEA: propylene glycol monomethyl ether acetate
EL: ethyl lactate
MPM: methoxymethyl propionate
CyPn: cyclopentanone
CyHe: cyclohexanone
γBL: γ-butyrolactone
DIAE: diisoamyl ether
nBA: butyl acetate
iAA: isoamyl acetate
Hexane: hexane
MAK: 2-heptanone
IPA: isopropanol
BHT: dibutylhydroxytoluene
Amylene: amylene (another name: 2-methyl-2-butene)
HQ: hydroquinone
DLTP: dilauryl thiodipropionate
DSTP: distearyl thiodipropionate
DMTP: dimyristyl thiodipropionate
A1: 4,4'-butylidenebis-(6-t-butyl-3-methylphenol)
A2: 2,2'-methylenebis-(4-ethyl-6-t-butylphenol)

[Type and Content of Organic Solvent and Stabilizer]

The type and the content of the organic solvent and the stabilizer in the substance to be purified were measured using a gas chromatography mass spectrometer (trade name: "GCMS-2020", Shimadzu Corporation) under the following conditions.

Capillary column: InertCap 5MS/NP 0.25 mm I.D.×30 m df=0.25 μm
Sample introduction method: split 75 kPa constant pressure
Vaporizing chamber temperature: 230° C.
Column oven temperature: 80° C. (2 min)-500° C. (13 min) heating rate 15° C./min
Carrier gas: helium
Septum purge flow rate: 5 mL/min
Split ratio: 25:1
Interface temperature: 250° C.
Ion source temperature: 200° C.
Measurement mode: Scan m/z=85~3,000
Amount of sample introduced: 1 μL

[Content of Metal Impurities by Type]

The content of metal impurities (metal ions and metal particles) in the substance to be purified was measured by type by using ICP-MS ("Agilent 8800 triple quadrupole ICP-MS (for semiconductor analysis, option #200)") under the following conditions.

As a sample introduction system, a quartz torch, a coaxial perfluoroalkoxyalkane (PFA) nebulizer (for self-suction), and a platinum interface cone were used. The measurement parameters of cool plasma conditions are as below.

Output of Radio Frequency (RF) (W): 600
Flow rate of carrier gas (L/min): 0.7
Flow rate of makeup gas (L/min): 1
Sampling depth (mm): 18

[Content of Water]

The content of water contained in the substance to be purified was measured using a Karl Fischer moisture meter (trade name "MKC-710M", manufactured by KYOTO ELECTRONICS MANUFACTURING CO., LTD., Karl Fischer coulometric titration method) under the room temperature condition.

[Purification of Substance to be Purified]

The substance to be purified was purified by any of the following methods. In Table 1, which purification method is used in each example is shown in the column of "Purification method".

"Filtration_A"

For purifying the substance to be purified, a device (device illustrated in FIG. 1) was used in which a manufacturing tank, a filter unit, and a filling device were connected to each other in this order through a pipe line.

The filter unit accommodated a filter cartridge. As the filter included in the filter cartridge, a filter was used which was made of PTFE, had a pore size of 10 nm, had a porous membrane-like pore structure, and had not been subjected to a surface treatment such as hydrophilization.

At the time of filtering the substance to be purified, a method was used in which the entirety of the substance to be purified was passed once through the aforementioned filter (method in which circulation filtration was not performed).

"Filtration_B"

For purifying the substance to be purified, a filtering device was used which was obtained by adding one more filter unit to the filtering device illustrated in FIG. 1 and arranging a total of two filter units in series in the pipe line (in the direction along which the substance to be purified flows).

The same filter cartridge as that used in "Filtration_A" was accommodated in the filter unit on the primary side.

A filter unit different from the above filter unit was accommodated in the filter unit on the secondary side. As the filter included in this filter unit, a filter was used which was made of nylon, had a pore size of 5 nm, had a porous membrane-like pore structure, and had not been subjected to a surface treatment such as hydrophilization.

At the time of filtering the substance to be purified, a method was used in which the entirety of the substance to be purified was passed once through each of two filters described above (method in which circulation filtration was not performed).

"Filtration_C"

For purifying the substance to be purified, the same filtering device and filter cartridge as those used in "Filtration_A" were used.

The substance to be purified was subjected to circulation filtration. That is, a method was used in which the substance to be purified having passed through the filter unit was sent back to the manufacturing tank and passes again through the filter unit. The substance to be purified was circulated 10 times.

"Ion Exchange"

For purifying the substance to be purified, a purification device was used in which the filtering device shown in FIG. 1 had a resin column filled with an ion exchange resin instead of the filter unit.

The resin column was filled with an ion exchange resin ("MSPS2-1-DRY" manufactured by ORGANO CORPORATION).

At the time of purifying the substance to be purified, a method was used in which the entirety of the substance to be purified was passed once through the resin column.

"Ion adsorption" For purifying the substance to be purified, a purification device was used in which the filtering device shown FIG. 1 had a resin column filled with an ion adsorption resin instead of the filter unit.

The resin column was filled with an ion adsorption resin ("CHELEST FIBER" manufactured by CHELEST CORPORATION).

At the time of purifying the substance to be purified, a method was used in which the entirety of the substance to be purified was passed once through the resin column.

"Distillation-ion exchange" The substance to be purified was purified by the same method as that in "Ion exchange", except that in the purification device used in "Ion exchange" described above, a distillation device having a distillation column on a primary side of the resin tower was used.

[Composition of Chemical Liquid]

The content of the stabilizer and the metal impurities in the chemical liquid was measured by the same method as that used for measuring the content of the stabilizer and the metal impurities in the substance to be purified. The results are shown in Table 1.

[Evaluation of Particle Defect Inhibition Performance of Chemical Liquid]

The particle defect inhibition performance of each of the chemical liquids was evaluated by the following method. The results are shown in Table 1.

First, a silicon oxide film substrate having a diameter of 300 mm was prepared.

Then, by using a wafer surface inspection device (SP-5; manufactured by KLA-Tencor Corporation.), the number of particles having a diameter equal to or greater than 19 nm that were present on the substrate was counted. Subsequently, the coordinates of the defects obtained as a result of the measurement described above were read, and the composition of each of the defects was investigated by energy dispersive X-ray (EDX) analysis. The number of defects containing metal components among the aforementioned particles was adopted as the number of particle defects and named initial value. Thereafter, the substrate was set in a spin jetting device, and while the substrate was being rotated, each of the chemical liquids was jetted to the surface of the substrate at a flow rate of 1.5 L/min. Then, the substrate was spin-dried.

Then, by using the device (SP-5), the number of defects present on the substrate after being coated with the chemical liquid was counted. In the same manner as that described above, the number of defects containing metal components was adopted as the number of particle defects and named counted value. Based on the following standards, the obtained results were evaluated. The results are shown in the column of "Particle defect" in Table 1.

"AA": The difference between the initial value of the number of particle defects and the counted value of the number of particle defects was equal to or smaller than 100.

"A": The difference between the initial value of the number of particle defects and the counted value of the number of particle defects was greater than 100 and equal to or smaller than 300.

"B": The difference between the initial value of the number of particle defects and the counted value of the number of particle defects was greater than 300 and equal to or smaller than 500.

"C": The difference between the initial value of the number of particle defects and the counted value of the number of particle defects was greater than 500 and equal to or smaller than 1,000.

"D": The difference between the initial value of the number of particle defects and the counted value of the number of particle defects was greater than 1,000.

[Evaluation of Stain-Like Defect Inhibition Performance of Chemical Liquid]

The stain-like defect inhibition performance of each of the chemical liquids was evaluated by the following method. The results are shown in Table 1. The coordinates of the defects obtained as a result of measuring the particle defect inhibition performance were read, and the composition of each of the defects was investigated by EDX analysis. The defects that did not contain metal components were defined as strain-like defects, and the result was evaluated based on the following standards.

"AA": The difference between the initial value of the number of stain-like defects and the counted value of the number of stain-like defects was equal to or smaller than 80.

"A": The difference between the initial value of the number of stain-like defects and the counted value of the number of stain-like defects was greater than 80 and equal to or smaller than 200.

"B": The difference between the initial value of the number of stain-like defects and the counted value of the number of stain-like defects was greater than 200 and equal to or smaller than 300.

"C": The difference between the counted value of the number of stain-like defects and the initial value of the number of stain-like defects was greater than 300 and equal to or smaller than 500.

"D": The difference between the counted value of the number of stain-like defects and the initial value of the number of stain-like defects was greater than 500.

Example 1A: Preparation of Resist Composition (Actinic Ray-Sensitive or Radiation-Sensitive Composition)

By mixing the following components together, a resist composition for EUV was prepared.
Resin: A-2, 0.79 g
Acid generator: B-2, 0.18 g
Basic compound: E-1, 0.03 g
Solvent: chemical liquid of Example 1, 75 g The resin A-2 is a resin constituted with the units represented by the following formulae.

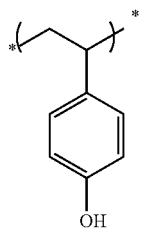 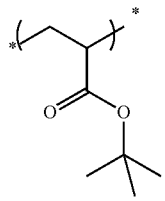

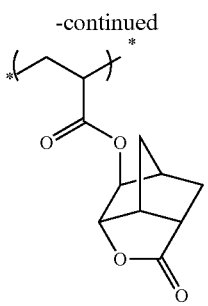

The contents of the units in the resin A-2 is 30:60:10 from left in terms of molar ratio. The weight-average molecular weight thereof is 12,300, and Mw/Mn thereof is 1.51.

The acid generator B-2 is a compound represented by the following formula.

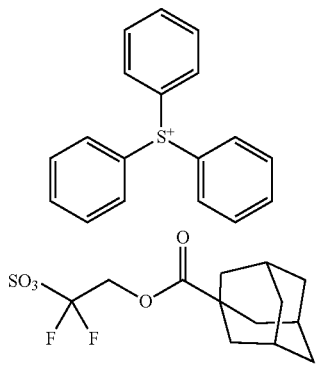

The basic compound E-1 is a compound represented by the following formula.

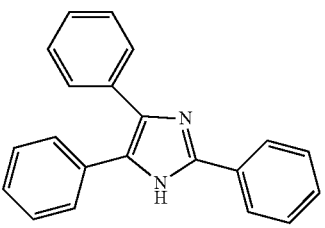 [SMILES: c1ccc(-c2nc(-c3ccccc3)c(-c3ccccc3)[nH]2)cc1]

Examples 2A and 3A: Preparation of Resist Composition

Resist compositions of Example 2A and Example 3A were prepared in the same manner as the manner adopted for preparing the chemical liquid of Example 1A, except that the chemical liquids of Example 25 and Example 42 were used instead of the chemical liquid of Example 1.

[Defect Inhibition Performance of Resist Composition]

Regarding the defect inhibition performance of the resist compositions prepared as above, the particle defect inhibition performance and the stain-like defect inhibition performance of the resist compositions were evaluated by the same method as that described above. As a result, the evaluation results of the defect inhibition performance relating to the resist compositions of Examples 1A to 3A were the same as the evaluation results of the chemical liquid of Example 1, Example 25, and Example 42.

Examples 1B to 3B: Preparation and Evaluation of Color Mosaic Solution

PGMEA contained in the colored radiation-sensitive composition G-1 described in JP2013-015817A was replaced with the chemical liquid of Example 1, thereby preparing a color mosaic solution (resist composition containing a colorant) (Example 1B).

In the same manner as that described above, PGMEA described above was replaced with the chemical liquid of Example 25 and the chemical liquid of Example 42, thereby preparing color mosaic solutions (Examples 2B and 3B).

By the same method as that described above, the defect inhibition performance of the color mosaic solutions of Examples 1B to 3B was evaluated. The results from Examples 1B, 2B, and 3B were the same as the results from Example 1, Example 25, and Example 42 respectively.

Example 1C: Preparation and Evaluation of p-CMP Rinsing Solution (Washing Solution Used after CMP)

The chemical liquid of Example 15 was used as a p-CMP rinsing solution. That is, a substrate having undergone CMP was washed with "Clean 100" manufactured by Wako Pure Chemical Industries, Ltd. and the chemical liquid described above, and the defect inhibition performance of the obtained substrate having undergone washing was evaluated by the same method as that described above. The results from this substrate were the same as the evaluation results from Example 15.

TABLE 1

Table 1-1-1

| | Composition of substance to be purified | | | |
|---|---|---|---|---|
| | Organic solvent | | Stabilizer | Content |
| | Type | Content (based on mass) | Type | Content (mass ppm) | of water (mass ppm) |
| Example 1 | PGMM | Balance | BHT | 3.0 | 5,000 |
| Example 2 | PGME | Balance | BHT | 2.0 | 3,333 |
| Example 3 | PGMP | Balance | BHT | 4.0 | 6,667 |
| Example 4 | PGMEA | Balance | BHT | 3.0 | 5,000 |
| Example 5 | EL | Balance | BHT | 3.0 | 5,000 |
| Example 6 | MPM | Balance | BHT | 4.0 | 6,667 |
| Example 7 | CyPn | Balance | BHT | 5.0 | 8,333 |
| Example 8 | CyHe | Balance | BHT | 3.0 | 5,000 |
| Example 9 | γBL | Balance | BHT | 2.0 | 3,333 |
| Example 10 | DIAE | Balance | BHT | 3.0 | 5,000 |
| Example 11 | nBA | Balance | BHT | 4.0 | 6,667 |
| Example 12 | iAA | Balance | BHT | 6.0 | 10,000 |
| Example 13 | Hexane | Balance | BHT | 3.0 | 5,000 |
| Example 14 | MAK | Balance | BHT | 4.0 | 6,667 |
| Example 15 | IPA | Balance | BHT | 3.0 | 5,000 |
| Example 16 | PGMEA/PGME (V/V = 7/3) | Balance | BHT | 6.0 | 10,000 |
| Example 17 | PGMEA | Balance | BHT | 3.0 | 100 |
| Example 18 | PGMEA | Balance | BHT | 3.0 | 500 |
| Example 19 | PGMEA | Balance | BHT | 3.0 | 15,000 |
| Example 20 | PGMEA | Balance | BHT | 3.0 | 30,000 |
| Example 21 | PGMEA | Balance | BHT | 3.0 | 52,000 |
| Example 22 | PGMEA | Balance | BHT | 0.10 | 5,400 |
| Example 23 | PGMEA | Balance | BHT | 0.50 | 6,000 |
| Example 24 | PGMEA | Balance | BHT | 10 | 10,000 |

TABLE 1-continued

Table 1-1-1

| | Composition of substance to be purified | | | | |
|---|---|---|---|---|---|
| | Organic solvent | | Stabilizer | | Content |
| | Type | Content (based on mass) | Type | Content (mass ppm) | of water (mass ppm) |
| Example 25 | PGMEA | Balance | BHT | 50 | 10,000 |
| Example 26 | PGMEA | Balance | BHT | 95 | 10,000 |
| Example 27 | PGMEA | Balance | BHT | 3.0 | 5,000 |
| Example 28 | PGMEA | Balance | BHT | 3.0 | 5,000 |
| Example 29 | PGMEA | Balance | BHT | 3.0 | 5,000 |
| Example 30 | PGMEA | Balance | BHT | 3.0 | 5,000 |
| Example 31 | PGMEA | Balance | Amylene | 3.0 | 5,000 |

TABLE 2

Table 1-1-2

| | Composition of substance to be purified Metal impurities Metal ions | | | |
|---|---|---|---|---|
| | Fe (mass ppt) | Cr (mass ppt) | Ni (mass ppt) | Pb (mass ppt) |
| Example 1 | 48.0 | 72.0 | 43.2 | 57.6 |
| Example 2 | 72.0 | 108 | 64.8 | 86.4 |
| Example 3 | 64.0 | 96.0 | 57.6 | 76.8 |
| Example 4 | 56.0 | 84.0 | 50.4 | 67.2 |
| Example 5 | 48.0 | 72.0 | 43.2 | 57.6 |
| Example 6 | 64.0 | 96.0 | 57.6 | 76.8 |
| Example 7 | 80.0 | 120 | 72.0 | 96.0 |
| Example 8 | 72.0 | 108 | 64.8 | 86.4 |
| Example 9 | 56.0 | 84.0 | 50.4 | 67.2 |
| Example 10 | 72.0 | 108 | 64.8 | 86.4 |
| Example 11 | 48.0 | 72.0 | 43.2 | 57.6 |
| Example 12 | 64.0 | 96.0 | 57.6 | 76.8 |
| Example 13 | 56.0 | 84.0 | 50.4 | 67.2 |
| Example 14 | 72.0 | 108 | 64.8 | 86.4 |
| Example 15 | 64.0 | 96.0 | 57.6 | 76.8 |
| Example 16 | 72.0 | 108 | 64.8 | 86.4 |
| Example 17 | 72.0 | 36.0 | 57.6 | 21.6 |
| Example 18 | 81.0 | 40.5 | 64.8 | 24.3 |
| Example 19 | 101 | 50.5 | 80.8 | 30.3 |
| Example 20 | 109 | 54.5 | 87.2 | 32.7 |
| Example 21 | 136 | 68.0 | 109 | 40.8 |
| Example 22 | 23.0 | 11.5 | 18.4 | 6.9 |
| Example 23 | 30.0 | 15.0 | 24.0 | 9.0 |
| Example 24 | 78.0 | 39.0 | 62.4 | 23.4 |
| Example 25 | 156 | 78.0 | 125 | 46.8 |
| Example 26 | 198 | 99.0 | 158 | 59.4 |
| Example 27 | 19.2 | 9.6 | 15.4 | 5.8 |
| Example 28 | 24.0 | 12.0 | 19.2 | 7.2 |

TABLE 2-continued

Table 1-1-2

| | Composition of substance to be purified Metal impurities Metal ions | | | |
|---|---|---|---|---|
| | Fe (mass ppt) | Cr (mass ppt) | Ni (mass ppt) | Pb (mass ppt) |
| Example 29 | 52.2 | 26.1 | 41.8 | 15.7 |
| Example 30 | 39.2 | 19.6 | 31.4 | 11.8 |
| Example 31 | 36.3 | 18.1 | 29.0 | 10.9 |

TABLE 3

Table 1-1-3

| | Composition of substance to be purified Metal impurities Metal particles | | | |
|---|---|---|---|---|
| | Fe (mass ppt) | Cr (mass ppt) | Ni (mass ppt) | Pb (mass ppt) |
| Example 1 | 16.0 | 14.4 | 7.2 | 11.5 |
| Example 2 | 24.0 | 21.6 | 10.8 | 17.3 |
| Example 3 | 21.3 | 19.2 | 9.6 | 15.4 |
| Example 4 | 18.7 | 16.8 | 8.4 | 13.4 |
| Example 5 | 16.0 | 14.4 | 7.2 | 11.5 |
| Example 6 | 21.3 | 19.2 | 9.6 | 15.4 |
| Example 7 | 26.7 | 24.0 | 12.0 | 19.2 |
| Example 8 | 24.0 | 21.6 | 10.8 | 17.3 |
| Example 9 | 18.7 | 16.8 | 8.4 | 13.4 |
| Example 10 | 24.0 | 21.6 | 10.8 | 17.3 |
| Example 11 | 16.0 | 14.4 | 7.2 | 11.5 |
| Example 12 | 21.3 | 19.2 | 9.6 | 15.4 |
| Example 13 | 18.7 | 16.8 | 8.4 | 13.4 |
| Example 14 | 24.0 | 21.6 | 10.8 | 17.3 |
| Example 15 | 21.3 | 19.2 | 9.6 | 15.4 |
| Example 16 | 24.0 | 21.6 | 10.8 | 17.3 |
| Example 17 | 18.0 | 9.0 | 14.4 | 5.4 |
| Example 18 | 20.3 | 10.1 | 16.2 | 6.1 |
| Example 19 | 25.3 | 12.6 | 20.2 | 7.6 |
| Example 20 | 27.3 | 13.6 | 21.8 | 8.2 |
| Example 21 | 34.0 | 17.0 | 27.2 | 10.2 |
| Example 22 | 5.8 | 2.9 | 4.6 | 1.7 |
| Example 23 | 7.5 | 3.8 | 6.0 | 2.3 |
| Example 24 | 19.5 | 9.8 | 15.6 | 5.9 |
| Example 25 | 39.0 | 19.5 | 31.2 | 11.7 |
| Example 26 | 49.5 | 24.8 | 39.6 | 14.9 |
| Example 27 | 4.8 | 2.4 | 3.8 | 1.4 |
| Example 28 | 6.0 | 3.0 | 4.8 | 1.8 |
| Example 29 | 13.1 | 6.5 | 10.4 | 3.9 |
| Example 30 | 9.8 | 4.9 | 7.8 | 2.9 |
| Example 31 | 9.1 | 4.5 | 7.3 | 2.7 |

TABLE 4

Table 1-1-4

| | | Composition of chemical liquid | | | | |
|---|---|---|---|---|---|---|
| | | Content of | Metal impurities Metal ions | | | |
| | Purification method | stabilizer (mass ppm) | Fe (mass ppt) | Cr (mass ppt) | Ni (mass ppt) | Pb (mass ppt) |
| Example 1 | Filtration_B | 2.94 | 4.8 | 7.2 | 4.3 | 5.8 |
| Example 2 | Filtration_B | 1.96 | 7.2 | 10.8 | 6.5 | 8.6 |
| Example 3 | Filtration_B | 3.92 | 6.4 | 9.6 | 5.8 | 7.7 |
| Example 4 | Filtration_B | 2.94 | 5.6 | 8.4 | 5.0 | 6.7 |
| Example 5 | Filtration_B | 2.94 | 4.8 | 7.2 | 4.3 | 5.8 |
| Example 6 | Filtration_B | 3.92 | 6.4 | 9.6 | 5.8 | 7.7 |
| Example 7 | Filtration_B | 4.9 | 8.0 | 12.0 | 7.2 | 9.6 |
| Example 8 | Filtration_B | 2.94 | 7.2 | 10.8 | 6.5 | 8.6 |

TABLE 4-continued

| Table 1-1-4 | Purification method | Content of stabilizer (mass ppm) | Fe (mass ppt) | Cr (mass ppt) | Ni (mass ppt) | Pb (mass ppt) |
|---|---|---|---|---|---|---|
| Example 9 | Filtration_B | 1.96 | 5.6 | 8.4 | 5.0 | 6.7 |
| Example 10 | Filtration_B | 2.94 | 7.2 | 10.8 | 6.5 | 8.6 |
| Example 11 | Filtration_B | 3.92 | 4.8 | 7.2 | 4.3 | 5.8 |
| Example 12 | Filtration_B | 5.88 | 6.4 | 9.6 | 5.8 | 7.7 |
| Example 13 | Filtration_B | 2.94 | 5.6 | 8.4 | 5.0 | 6.7 |
| Example 14 | Filtration_B | 3.92 | 7.2 | 10.8 | 6.5 | 8.6 |
| Example 15 | Filtration_B | 2.94 | 6.4 | 9.6 | 5.8 | 7.7 |
| Example 16 | Filtration_B | 5.88 | 7.2 | 10.8 | 6.5 | 8.6 |
| Example 17 | Filtration_B | 2.94 | 7.2 | 3.6 | 5.8 | 2.2 |
| Example 18 | Filtration_B | 2.94 | 8.1 | 4.1 | 6.5 | 2.4 |
| Example 19 | Filtration_B | 2.94 | 10.1 | 5.1 | 8.1 | 3.0 |
| Example 20 | Filtration_B | 2.94 | 10.9 | 5.5 | 8.7 | 3.3 |
| Example 21 | Filtration_B | 2.94 | 13.6 | 6.8 | 10.9 | 4.1 |
| Example 22 | Filtration_B | 0.10 | 2.3 | 1.2 | 1.8 | 0.7 |
| Example 23 | Filtration_B | 0.50 | 3.0 | 1.5 | 2.4 | 0.9 |
| Example 24 | Filtration_B | 9.8 | 7.8 | 3.9 | 6.2 | 2.3 |
| Example 25 | Filtration_B | 49 | 15.6 | 7.8 | 12.5 | 4.7 |
| Example 26 | Filtration_B | 93.1 | 19.8 | 9.9 | 15.8 | 5.9 |
| Example 27 | Ion exchange | 2.94 | 4.8 | 2.4 | 3.8 | 1.4 |
| Example 28 | Ion adsorption | 2.45 | 4.0 | 2.0 | 3.2 | 1.2 |
| Example 29 | Distillation · Ion exchange | 0.03 | 5.8 | 2.9 | 4.6 | 1.7 |
| Example 30 | Filtration_C | 2.94 | 5.6 | 2.8 | 4.5 | 1.7 |
| Example 31 | Filtration_C | 2.94 | 5.2 | 2.6 | 4.1 | 1.6 |

TABLE 5

| Table 1-1-5 | Fe (mass ppt) | Cr (mass ppt) | Ni (mass ppt) | Pb (mass ppt) | Stain-like defects | Particle defects |
|---|---|---|---|---|---|---|
| Example 1 | 1.6 | 1.4 | 0.7 | 1.2 | AA | AA |
| Example 2 | 2.4 | 2.2 | 1.1 | 1.7 | AA | AA |
| Example 3 | 2.1 | 1.9 | 1.0 | 1.5 | AA | AA |
| Example 4 | 1.9 | 1.7 | 0.8 | 1.3 | AA | AA |
| Example 5 | 1.6 | 1.4 | 0.7 | 1.2 | AA | AA |
| Example 6 | 2.1 | 1.9 | 1.0 | 1.5 | AA | AA |
| Example 7 | 2.7 | 2.4 | 1.2 | 1.9 | AA | AA |
| Example 8 | 2.4 | 2.2 | 1.1 | 1.7 | AA | AA |
| Example 9 | 1.9 | 1.7 | 0.8 | 1.3 | AA | AA |
| Example 10 | 2.4 | 2.2 | 1.1 | 1.7 | AA | AA |
| Example 11 | 1.6 | 1.4 | 0.7 | 1.2 | AA | AA |
| Example 12 | 2.1 | 1.9 | 1.0 | 1.5 | AA | AA |
| Example 13 | 1.9 | 1.7 | 0.8 | 1.3 | AA | AA |
| Example 14 | 2.4 | 2.2 | 1.1 | 1.7 | AA | AA |
| Example 15 | 2.1 | 1.9 | 1.0 | 1.5 | AA | AA |
| Example 16 | 2.4 | 2.2 | 1.1 | 1.7 | AA | AA |
| Example 17 | 1.8 | 0.9 | 1.4 | 0.5 | B | AA |
| Example 18 | 2.0 | 1.0 | 1.6 | 0.6 | A | AA |
| Example 19 | 2.5 | 1.3 | 2.0 | 0.8 | AA | AA |
| Example 20 | 2.7 | 1.4 | 2.2 | 0.8 | AA | A |
| Example 21 | 3.4 | 1.7 | 2.7 | 1.0 | AA | B |
| Example 22 | 0.6 | 0.3 | 0.5 | 0.2 | AA | C |
| Example 23 | 0.8 | 0.4 | 0.6 | 0.2 | AA | A |
| Example 24 | 2.0 | 1.0 | 1.6 | 0.6 | A | AA |
| Example 25 | 3.9 | 2.0 | 3.1 | 1.2 | B | AA |
| Example 26 | 5.0 | 2.5 | 4.0 | 1.5 | C | AA |
| Example 27 | 1.2 | 0.6 | 1.0 | 0.4 | AA | AA |
| Example 28 | 1.0 | 0.5 | 0.8 | 0.3 | AA | AA |
| Example 29 | 1.5 | 0.7 | 1.2 | 0.4 | A | B |
| Example 30 | 1.4 | 0.7 | 1.1 | 0.4 | AA | AA |
| Example 31 | 1.3 | 0.6 | 1.0 | 0.4 | AA | AA |

TABLE 6

Table 1-2-1

| | Composition of substance to be purified | | | | |
|---|---|---|---|---|---|
| | Organic solvent | | Stabilizer | | Content of water (mass ppm) |
| | Type | Content (based on mass) | Type | Content (mass ppm) | |
| Example 32 | PGMEA | Balance | Amylene | 3.0 | 5,000 |
| Example 33 | PGMEA | Balance | HQ | 3.0 | 5,000 |
| Example 34 | PGMEA | Balance | DLTP | 3.0 | 5,000 |
| Example 35 | PGMEA | Balance | DSTP | 3.0 | 5,000 |
| Example 36 | PGMEA | Balance | DMTP | 3.0 | 5,000 |
| Example 37 | PGMEA | Balance | A1 | 3.0 | 5,000 |
| Example 38 | PGMEA | Balance | A2 | 3.0 | 5,000 |
| Example 39 | PGMEA | Balance | BHT | 3.0 | 5,000 |
| Example 40 | PGMEA | Balance | BHT | 3.0 | 5,000 |
| Example 41 | PGMEA | Balance | BHT | 3.0 | 5,000 |
| Example 42 | PGMEA | Balance | BHT | 3.0 | 5,000 |
| Example 43 | PGMEA | Balance | BHT | 3.0 | 5,000 |
| Example 44 | PGMEA | Balance | BHT | 3.0 | 5,000 |
| Example 45 | PGMEA | Balance | BHT | 3.0 | 5,000 |
| Example 46 | PGMEA | Balance | BHT | 3.0 | 5,000 |
| Example 47 | PGMEA | Balance | BHT | 3.0 | 5,000 |
| Example 48 | PGMEA | Balance | BHT | 3.0 | 5,000 |
| Example 49 | PGMEA | Balance | BHT | 3.0 | 5,000 |
| Example 50 | PGMEA | Balance | BHT | 3.0 | 5,000 |
| Example 51 | PGMEA | Balance | BHT | 3.0 | 5,000 |
| Comparative Example 1 | PGMEA | Balance | BHT | 0.05 | 83 |
| Comparative Example 2 | PGMEA | Balance | BHT | 105 | 175,000 |

TABLE 7

Table 1-2-2

| | Composition of substance to be purified Metal impurities Metal ions | | | |
|---|---|---|---|---|
| | Fe (mass ppt) | Cr (mass ppt) | Ni (mass ppt) | Pb (mass ppt) |
| Example 32 | 36.3 | 18.1 | 29.0 | 10.9 |
| Example 33 | 54.4 | 27.2 | 43.5 | 16.3 |
| Example 34 | 34.6 | 17.3 | 27.6 | 10.4 |
| Example 35 | 30.2 | 15.1 | 24.2 | 9.1 |
| Example 36 | 25.9 | 13.0 | 20.7 | 7.8 |
| Example 37 | 34.6 | 76.8 | 25.6 | 19.2 |
| Example 38 | 43.2 | 96.0 | 32.0 | 24.0 |
| Example 39 | 72.0 | 57.6 | 43.2 | 0.6 |
| Example 40 | 70.0 | 59.0 | 45.2 | 47.0 |
| Example 41 | 84.0 | 126 | 75.6 | 101 |
| Example 42 | 448 | 672 | 403 | 538 |
| Example 43 | 1680 | 2520 | 1512 | 2016 |
| Example 44 | 5600 | 8400 | 5040 | 6720 |
| Example 45 | 16800 | 25200 | 15120 | 20160 |
| Example 46 | 33.6 | 16.8 | 26.9 | 10.1 |
| Example 47 | 35.7 | 17.9 | 28.6 | 10.7 |
| Example 48 | 37.1 | 18.6 | 29.7 | 11.1 |
| Example 49 | 41.3 | 20.7 | 33.0 | 12.4 |
| Example 50 | 47.6 | 23.8 | 38.1 | 14.3 |
| Example 51 | 48.3 | 23.1 | 39.9 | 19.6 |
| Comparative Example 1 | 8.6 | 4.3 | 6.9 | 2.6 |
| Comparative Example 2 | 65.0 | 32.5 | 52.0 | 19.5 |

TABLE 8

Table 1-2-3

| | Composition of substance to be purified Metal impurities Metal particles | | | |
|---|---|---|---|---|
| | Fe (mass ppt) | Cr (mass ppt) | Ni (mass ppt) | Pb (mass ppt) |
| Example 32 | 9.1 | 4.5 | 7.3 | 2.7 |
| Example 33 | 13.6 | 6.8 | 10.9 | 4.1 |
| Example 34 | 8.6 | 4.3 | 6.9 | 2.6 |
| Example 35 | 7.6 | 3.8 | 6.0 | 2.3 |
| Example 36 | 6.5 | 3.2 | 5.2 | 1.9 |
| Example 37 | 11.5 | 25.6 | 8.5 | 6.4 |
| Example 38 | 14.4 | 32.0 | 10.7 | 8.0 |
| Example 39 | 22.0 | 18.2 | 8.5 | 11.0 |
| Example 40 | 12.8 | 15.0 | 6.9 | 0.9 |
| Example 41 | 9.3 | 8.4 | 4.2 | 6.7 |
| Example 42 | 9.3 | 8.4 | 4.2 | 6.7 |
| Example 43 | 9.3 | 8.4 | 4.2 | 6.7 |
| Example 44 | 9.3 | 8.4 | 4.2 | 6.7 |
| Example 45 | 9.3 | 8.4 | 4.2 | 6.7 |
| Example 46 | 28.0 | 25.2 | 12.6 | 20.2 |
| Example 47 | 149 | 134 | 67.2 | 108 |
| Example 48 | 560 | 504 | 252 | 403 |
| Example 49 | 1,867 | 1,680 | 840 | 1,344 |
| Example 50 | 5,600 | 5,040 | 2,520 | 4,032 |
| Example 51 | 10,200 | 7,510 | 4,500 | 7,800 |
| Comparative Example 1 | 2.2 | 1.1 | 1.7 | 0.6 |
| Comparative Example 2 | 16.3 | 8.1 | 13.0 | 4.9 |

TABLE 9

Table 1-2-4

| | | Composition of chemical liquid | | | | |
|---|---|---|---|---|---|---|
| | | | Metal impurities Metal ions | | | |
| | Purification method | Content of stabilizer (mass ppm) | Fe (mass ppt) | Cr (mass ppt) | Ni (mass ppt) | Pb (mass ppt) |
| Example 32 | Filtration_C | 2.94 | 5.2 | 2.6 | 4.1 | 1.6 |
| Example 33 | Filtration_C | 2.94 | 7.8 | 3.9 | 6.2 | 2.3 |
| Example 34 | Filtration_C | 2.94 | 6.9 | 3.5 | 5.5 | 2.1 |
| Example 35 | Filtration_D | 2.94 | 6.0 | 3.0 | 4.8 | 1.8 |
| Example 36 | Filtration_D | 2.94 | 5.2 | 2.6 | 4.1 | 1.6 |

TABLE 9-continued

| | | Composition of chemical liquid | | | | |
|---|---|---|---|---|---|---|
| | | Content of | Metal impurities Metal ions | | | |
| Table 1-2-4 | Purification method | stabilizer (mass ppm) | Fe (mass ppt) | Cr (mass ppt) | Ni (mass ppt) | Pb (mass ppt) |
| Example 37 | Filtration_D | 2.94 | 6.9 | 15.4 | 5.1 | 3.8 |
| Example 38 | Filtration_D | 2.94 | 8.6 | 19.2 | 6.4 | 4.8 |
| Example 39 | Filtration_B | 2.94 | 6.9 | 5.2 | 4.1 | 0.5 |
| Example 40 | Filtration_B | 2.94 | 7.2 | 5.8 | 4.3 | 4.8 |
| Example 41 | Filtration_A | 2.94 | 16.8 | 25.2 | 15.1 | 20.2 |
| Example 42 | Filtration_A | 2.94 | 89.6 | 134 | 80.6 | 108 |
| Example 43 | Filtration_A | 2.94 | 336 | 504 | 302 | 403 |
| Example 44 | Filtration_A | 2.94 | 1,120 | 1,680 | 1,008 | 1,344 |
| Example 45 | Filtration_A | 2.94 | 3,360 | 5,040 | 3,024 | 4,032 |
| Example 46 | Filtration_A | 2.94 | 4.8 | 2.4 | 3.8 | 1.4 |
| Example 47 | Filtration_A | 2.94 | 5.1 | 2.6 | 4.1 | 1.5 |
| Example 48 | Filtration_A | 2.94 | 5.3 | 2.7 | 4.2 | 1.6 |
| Example 49 | Filtration_A | 2.94 | 5.9 | 3.0 | 4.7 | 1.8 |
| Example 50 | Filtration_A | 2.94 | 6.8 | 3.4 | 5.4 | 2.0 |
| Example 51 | Filtration_A | 2.94 | 6.9 | 3.3 | 5.7 | 2.8 |
| Comparative Example 1 | Filtration_B | 0.049 | 4.3 | 2.2 | 3.4 | 1.3 |
| Comparative Example 2 | Filtration_B | 103 | 32.5 | 16.3 | 26.0 | 9.8 |

TABLE 10

| | Composition of chemical liquid Metal impurities Metal particles | | | | Defect inhibition performance | |
|---|---|---|---|---|---|---|
| Table 1-2-5 | Fe (mass ppt) | Cr (mass ppt) | Ni (mass ppt) | Pb (mass ppt) | Stain-like defects | Particle defects |
| Example 32 | 1.3 | 0.6 | 1.0 | 0.4 | AA | AA |
| Example 33 | 1.9 | 1.0 | 1.6 | 0.6 | AA | AA |
| Example 34 | 1.7 | 0.9 | 1.4 | 0.5 | AA | AA |
| Example 35 | 1.5 | 0.8 | 1.2 | 0.5 | AA | AA |
| Example 36 | 1.3 | 0.6 | 1.0 | 0.4 | AA | AA |
| Example 37 | 2.3 | 5.1 | 1.7 | 1.3 | AA | AA |
| Example 38 | 2.9 | 6.4 | 2.1 | 1.6 | AA | AA |
| Example 39 | 12.4 | 14.2 | 7.2 | 9.5 | AA | A |
| Example 40 | 11.2 | 10.2 | 6.5 | 0.6 | AA | A |
| Example 41 | 1.9 | 1.7 | 0.8 | 1.3 | AA | A |
| Example 42 | 1.9 | 1.7 | 0.8 | 1.3 | AA | A |
| Example 43 | 1.9 | 1.7 | 0.8 | 1.3 | AA | B |
| Example 44 | 1.9 | 1.7 | 0.8 | 1.3 | AA | B |
| Example 45 | 1.9 | 1.7 | 0.8 | 1.3 | A | B |
| Example 46 | 4.0 | 3.6 | 1.8 | 2.9 | AA | A |
| Example 47 | 21.3 | 19.2 | 9.6 | 15.4 | AA | A |
| Example 48 | 80.0 | 72.0 | 36.0 | 57.6 | AA | B |
| Example 49 | 267 | 240 | 120 | 192 | A | B |
| Example 50 | 800 | 720 | 360 | 576 | B | B |
| Example 51 | 1,457 | 1,073 | 643 | 1,114 | C | C |
| Comparative Example 1 | 1.1 | 0.5 | 0.9 | 0.3 | AA | D |
| Comparative Example 2 | 8.1 | 4.1 | 6.5 | 2.4 | D | AA |

Table 1 is divided into a total of 10 tables consisting of 5 tables including Table 1-1-1 to Table 1-1-5 and 5 tables including Table 1-2-1 to Table 1-2-5.

The composition of the substance to be purified and the purification method used in each of examples and comparative examples, the composition of the obtained chemical liquid, and the evaluation results are described in the corresponding lines in Table 1-1-1 to Table 1-1-5 or in the corresponding lines in Table 1-2-1 to Table 1-2-S. Hereinafter, how to read what is described in each table will be explained.

For example, in the case of the chemical liquid purification method of Example 1, first, the used substance to be purified contained 3 mass ppm of BHT as a stabilizer, 5,000 mass ppm of water, and, as metal impurities, 48.0 mass ppt of Fe ions, 72.0 mass ppt of Cr ions, 43.2 mass ppt of Ni ions, 57.6 mass ppt of Pb ions, 16.0 mass ppt of Fe-containing metal particles, 14.4 mass ppt of Cr-containing metal particles, 7.2 mass ppt of Ni-containing metal particles, and 11.5 mass ppt of Pb-containing metal particles, and the balance was PGMM as an organic solvent. Furthermore, the "Filtration_B" was adopted as the purification method. The obtained chemical liquid contained 2.94 mass ppm as a stabilizer (BHT) and, as metal impurities, 4.8 mass ppt of Fe ions, 7.2 mass ppt of Cr ions, 4.3 mass ppt of Ni ions, 5.8 mass ppt of Pb ions, 1.6 mass ppt of Fe-containing metal particles, 1.4 mass ppt of Cr-containing metal particles, 0.7 mass ppt of Ni-containing metal particles, and 1.2 mass ppt of Pb-containing metal particles. Regarding the evaluation of the defect inhibition performance of the chemical liquid, the stain-like defects were graded "AA", and the particle defects were graded "AA".

For other examples and comparative examples, the tables can be read as described above.

As is evident from the results shown in Table 1, the chemical liquids obtained by the chemical liquid purification methods of the examples, in which the content of the stabilizer in the substance to be purified with respect to the total mass of the substance to be purified was equal to or greater than 0.1 mass ppm and less than 100 ppm, had the effects of the present invention. In contrast, the chemical liquids obtained by the chemical liquid purification methods of Comparative Examples 1 and 2 did not have the effects of the present invention.

The chemical liquid obtained by the chemical liquid purification method of Example 1, in which the substance to be purified contained water and the content of the water in the substance to be purified was equal to or greater than 500 mass ppm, had higher stain-like defect inhibition performance, compared to the chemical liquid obtained by the chemical liquid purification method of Example 17. Furthermore, the chemical liquid obtained by the chemical liquid purification method of Example 1, in which the substance to be purified contained water and the content of the water in the substance to be purified was equal to or smaller than 50,000 mass ppm, had higher particle defect inhibition performance, compared to the chemical liquid obtained by the chemical liquid purification method of Example 21.

The chemical liquid obtained by the chemical liquid purification method of Example 1, in which the substance to be purified contained specific metal ions and the content of each of the specific metal ions was equal to or greater than 1.0 mass ppt, had higher particle defect inhibition performance, compared to the chemical liquid obtained by the chemical liquid purification method of Example 39. Furthermore, the chemical liquid obtained by the chemical liquid purification method of Example 1, in which the substance to be purified contained specific metal ions and the content of each of the specific metal ions was equal to or smaller than 10,000 mass ppt, had higher particle defect inhibition performance, compared to the chemical liquid obtained by the chemical liquid purification method of Example 45.

The chemical liquid obtained by the chemical liquid purification method of Example 1, in which the substance to be purified contained specific metal particles and the content of the specific metal particles was equal to or greater than 1.0 mass ppt, had higher particle defect inhibition performance, compared to the chemical liquid obtained by the chemical liquid purification method of Example 40. Furthermore, the chemical liquid obtained by the chemical liquid purification method of Example 1, in which the substance to be purified contained specific metal particles and the content of the specific metal particles was equal to or smaller than 10,000 mass ppt, had higher defect inhibition performance, compared to the chemical liquid obtained by the chemical liquid purification method of Example 51.

The chemical liquid obtained by the chemical liquid purification method of Example 1, in which the content of the stabilizer in the chemical liquid was equal to or greater than 0.1 mass ppm, had higher particle defect inhibition performance, compared to the chemical liquids obtained by the chemical liquid purification methods of Examples 22 and 23. Furthermore, the chemical liquid obtained by the chemical liquid purification method of Example 1, in which the content of the stabilizer in the chemical liquid was equal to or smaller than 50 mass ppm, had higher stain-like defect inhibition performance, compared to the chemical liquid obtained by the chemical liquid purification method of Example 26.

The chemical liquid obtained by the chemical liquid purification method of Example 1, in which the content of the specific metal ions in the chemical liquid was equal to or smaller than 100 mass ppt, had higher particle defect inhibition performance, compared to the chemical liquid obtained by the chemical liquid purification method of Example 42. Furthermore, the chemical liquid obtained by the chemical liquid purification method of Example 1, in which the content of the specific metal particles in the chemical liquid was equal to or smaller than 100 mass ppt, had higher particle defect inhibition performance, compared to the chemical liquid obtained by the chemical liquid purification method of Example 49.

EXPLANATION OF REFERENCES

10: filtering device
11: manufacturing tank
12: filter unit
13: filling device
14, 14(a), and 14(b): pipe line
20: filter cartridge
21: filter
22: core
23: cap
24: liquid inlet
31: body
32: lid
34: liquid inlet
35: liquid outlet
41, 42: internal pipe line

What is claimed is:
1. A chemical liquid comprising:
an organic solvent;
a stabilizer;
at least one kind of metal ions selected from a group consisting of Fe, Cr, Pb, and Ni, and
at least one kind of metal particles selected from a group consisting of Fe, Cr, Pb, and Ni,
wherein a content of the stabilizer with respect to a total mass of the chemical liquid is 0.1 to 50 mass ppm,
in a case where the chemical liquid contains one kind of the at least one kind of metal ions, a content of the at least one kind of metal ions with respect to the total mass of the chemical liquid is equal to or smaller than 100 mass ppt,
in a case where the chemical liquid contains two or more kinds of the at least one kind of metal ions, a content of each of the at least one kind of metal ions with respect to the total mass of the chemical liquid is equal to or smaller than 100 mass ppt,
in a case where the chemical liquid contains one kind of the at least one kind of metal particles, a content of the at least one kind of metal particles with respect to the total mass of the chemical liquid is equal to or smaller than 100 mass ppt, and in a case where the chemical liquid contains two or more kinds of the at least one kind of metal particles, a content of each of the at least one kind of metal particles with respect to the total mass of the chemical liquid is equal to or smaller than 100 mass ppt.

2. A chemical liquid according to claim 1, wherein the chemical liquid comprises Pb ions and Pb particles.

3. A chemical liquid according to claim 1, wherein a content of the organic solvent with respect to the total mass of the chemical liquid is equal to or greater than 99.0%.

4. A chemical liquid according to claim 1, wherein the stabilizer is at least one compound selected from a group consisting of a compound represented by Formula (1), and a compound represented by Formula (2),

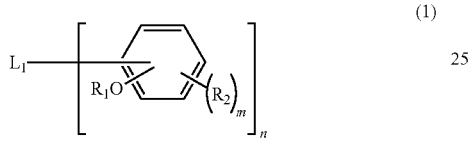
(1)

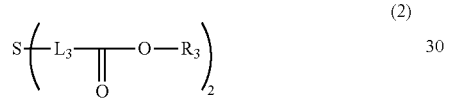
(2)

in Formula (1), m represents an integer of 1 to 4, and n represents an integer of 1 to 6, in a case where n is 1, $L_1$ represents a hydrogen atom, a hydroxyl group, or a monovalent organic group, $R_1$ represents a hydrogen atom, $R_2$ represents a hydrogen atom, a hydroxyl group, or a monovalent organic group, and a plurality of $R_2$'s may be the same as or different from each other, in a case where n is 2 to 6, $L_1$ represents an n-valent linking group, $R_1$ represents a hydrogen atom or a monovalent organic group, although a plurality of $R_1$'s may be the same as or different from each other, at least one of $R_1$'s represents a hydrogen atom, $R_2$ represents a hydrogen atom, a hydroxyl group, or a monovalent organic group, and a plurality of $R_2$'s may be the same as or different from each other, and in Formula (2), $L_3$ represents a single bond or a divalent linking group, $R_3$ represents a monovalent organic group, and a plurality of $L_3$'s and $R_3$'s may be the same as or different from each other respectively.

5. A chemical liquid according to claim 1, wherein the stabilizer is at least one compound selected from a group consisting of dibutylhydroxytoluene, amylene, hydroquinone, dilauryl thiodipropionate, distearyl thiodipropionate, dimyristyl thiodipropionate, 4,4'-butylidenebis-(6-t-butyl-3-methylphenol), and 2,2'-methylenebis-(4-ethyl-6-t-butylphenol).

6. A chemical liquid according to claim 1, wherein the organic solvent is at least one compound selected from a group consisting of propylene glycol monomethyl ether, propylene glycol monoethyl ether, propylene glycol monopropyl ether, propylene glycol monomethyl ether acetate, ethyl lactate, methoxymethyl propionate, cyclopentanone, cyclohexanone, γ-butyrolactone, diisoamyl ether, butyl acetate, isoamyl acetate, hexane, 2-heptanone, and isopropanol.

* * * * *